(12) United States Patent
Yurek et al.

(10) Patent No.: US 10,034,986 B2
(45) Date of Patent: Jul. 31, 2018

(54) METHOD AND APPARATUS OF TUBAL PATENCY CATHETER AND DELIVERY SYSTEMS

(71) Applicant: Cross Bay Medical, Inc., Irvine, CA (US)

(72) Inventors: Matt Yurek, San Diego, CA (US); Steven R. Bacich, Half Moon Bay, CA (US); Piush Vidyarthi, San Rafael, CA (US); Jack Greelis, Carlsbad, CA (US)

(73) Assignee: CrossBay Medical, Inc., San Diego, CA (US)

( * ) Notice: Subject to any disclaimer, the term of this patent is extended or adjusted under 35 U.S.C. 154(b) by 0 days.

(21) Appl. No.: 14/495,726

(22) Filed: Sep. 24, 2014

(65) Prior Publication Data

US 2015/0133779 A1     May 14, 2015

Related U.S. Application Data

(60) Provisional application No. 61/902,742, filed on Nov. 11, 2013, provisional application No. 61/977,478, (Continued)

(51) Int. Cl.
*A61M 11/00*     (2006.01)
*A61B 8/08*     (2006.01)
(Continued)

(52) U.S. Cl.
CPC ........... *A61M 11/008* (2014.02); *A61B 1/015* (2013.01); *A61B 8/12* (2013.01); *A61B 8/445* (2013.01); *A61B 8/481* (2013.01); *A61M 13/003* (2013.01); *A61M 25/003* (2013.01); *A61M 25/0068* (2013.01); *A61M 25/09016* (2013.01); *A61B 6/4057* (2013.01); *A61B 6/481* (2013.01); *A61B 8/488* (2013.01); *A61M 2025/0037* (2013.01); *A61M 2025/0073* (2013.01); *A61M 2210/1425* (2013.01); *A61M 2210/1433* (2013.01)

(58) Field of Classification Search
CPC .. A61M 5/141; A61M 5/2066; A61M 5/2448; A61M 5/284; A61M 11/00; A61M 11/008; A61M 16/14; A61M 25/003; A61M 25/0068; A61M 25/0071; A61M 2025/0037; A61M 2025/0073; A61M 2205/07; A61M 2205/071; A61M 2210/1433; A61B 6/481; A61B 8/481
See application file for complete search history.

(56) References Cited

U.S. PATENT DOCUMENTS 3,452,749 A     7/1969     Riedell
3,500,819 A     3/1970     Silverman
(Continued)

FOREIGN PATENT DOCUMENTS

WO     WO 1993/007927     4/1993
WO     WO 1994/025099     11/1994
(Continued)

*Primary Examiner* — Kami A Bosworth
(74) *Attorney, Agent, or Firm* — Levine Bagade Han LLP

(57) ABSTRACT

A method and apparatus for assessing bodily cavities and lumens utilizing an integrated, automated aerating device is described. The aeration device can selectively supply a gas a liquid during ultrasound and radiographic procedures for enhanced visualization of the uterine cavity and fallopian tubes.

20 Claims, 12 Drawing Sheets

Related U.S. Application Data filed on Apr. 9, 2014, provisional application No. 62/005,355, filed on May 30, 2014, provisional application No. 62/007,339, filed on Jun. 3, 2014.

(51) Int. Cl.

| | | |
|---|---|---|
| *A61M 25/00* | (2006.01) | |
| *A61M 25/09* | (2006.01) | |
| *A61B 8/12* | (2006.01) | |
| *A61B 8/00* | (2006.01) | |
| *A61B 1/015* | (2006.01) | |
| *A61M 13/00* | (2006.01) | |
| *A61B 6/00* | (2006.01) | |

(56) References Cited

U.S. PATENT DOCUMENTS

| | | | |
|---|---|---|---|
| 3,825,013 A | | 7/1974 | Craven |
| 3,911,927 A | | 10/1975 | Rich et al. |
| 3,982,544 A | | 9/1976 | Dyck |
| 4,271,839 A | | 6/1981 | Fogarty et al. |
| 4,654,027 A | | 3/1987 | Dragan et al. |
| 4,946,440 A | | 8/1990 | Hall |
| 5,211,627 A | | 5/1993 | William |
| 5,364,345 A | | 11/1994 | Lowery et al. |
| 5,374,247 A | | 12/1994 | Lowery et al. |
| 5,376,084 A | | 12/1994 | Bacich |
| 5,389,089 A | | 2/1995 | Bauer |
| 5,458,573 A | | 10/1995 | Summers |
| 5,531,219 A | | 7/1996 | Rosenberg |
| 5,630,797 A | | 5/1997 | Diedrich et al. |
| 5,662,582 A | | 9/1997 | Levius et al. |
| 5,724,994 A | | 3/1998 | Simon et al. |
| 5,925,058 A | | 7/1999 | Smith et al. |
| 5,954,688 A | | 9/1999 | Adams et al. |
| 5,964,223 A | * | 10/1999 | Baran ............... 128/207.14 |
| 6,039,721 A | | 3/2000 | Johnson et al. |
| 6,042,535 A | | 3/2000 | Porter |
| 6,080,129 A | * | 6/2000 | Blaisdell ............... 604/515 |
| 6,398,775 B1 | * | 6/2002 | Perkins ............ A61M 1/0058 |
| | | | 604/514 |
| 6,436,118 B1 | | 8/2002 | Kayan |
| 6,450,963 B1 | | 9/2002 | Ackerman |
| 6,729,334 B1 | | 5/2004 | Baran |
| 7,220,252 B2 | | 5/2007 | Shah |
| 7,556,060 B2 | | 7/2009 | Guala |
| 7,727,155 B2 | | 6/2010 | De Ziegler |
| 7,789,893 B2 | | 9/2010 | Drasler et al. |
| 8,551,001 B2 | | 10/2013 | Connor et al. |
| 9,326,790 B2 | | 5/2016 | Chin et al. |
| 2002/0108614 A1 | * | 8/2002 | Schultz ............... A61M 1/0047 |
| | | | 128/207.14 |
| 2003/0208223 A1 | | 11/2003 | Kleiner |
| 2004/0231668 A1 | * | 11/2004 | Kates ............... A61M 15/0085 |
| | | | 128/203.26 |
| 2005/0015047 A1 | | 1/2005 | Shah |
| 2005/0154415 A1 | | 7/2005 | Fogarty et al. |
| 2007/0203472 A1 | | 8/2007 | Nachmani |
| 2008/0167629 A1 | | 7/2008 | Dann et al. |
| 2009/0126731 A1 | * | 5/2009 | Dunsmore ......... A61M 16/0096 |
| | | | 128/203.12 |
| 2009/0293873 A1 | * | 12/2009 | Djupesland ....... A61M 15/0028 |
| | | | 128/203.15 |
| 2009/0299327 A1 | | 12/2009 | Tilson et al. |
| 2010/0086492 A1 | | 4/2010 | Lee-sepsick et al. |
| 2010/0147701 A1 | | 6/2010 | Field |
| 2011/0060276 A1 | | 3/2011 | Schaeffer et al. |
| 2011/0313400 A1 | | 12/2011 | Boatman |
| 2012/0035471 A1 | | 2/2012 | Lee-Sepsick et al. |
| 2012/0065674 A1 | | 3/2012 | Levy |
| 2012/0230915 A1 | | 9/2012 | Exalto et al. |
| 2013/0178785 A1 | | 7/2013 | Papay et al. |
| 2013/0253426 A1 | | 9/2013 | Campbell et al. |
| 2014/0114261 A1 | * | 4/2014 | Geppert et al. ............... 604/290 |
| 2014/0155745 A1 | | 6/2014 | Duncan |
| 2014/0166011 A1 | * | 6/2014 | Pierro ................ A61M 16/14 |
| | | | 128/204.14 |
| 2015/0040902 A1 | * | 2/2015 | Blum ................ A61M 11/041 |
| | | | 128/203.17 |
| 2017/0354437 A1 | | 12/2017 | Bacich |

FOREIGN PATENT DOCUMENTS

| | | |
|---|---|---|
| WO | WO 1997/021461 | 6/1997 |
| WO | WO 2009/042621 | 4/2009 |
| WO | WO 2010/055701 | 6/2010 |
| WO | WO 2015/069952 | 5/2015 |

\* cited by examiner

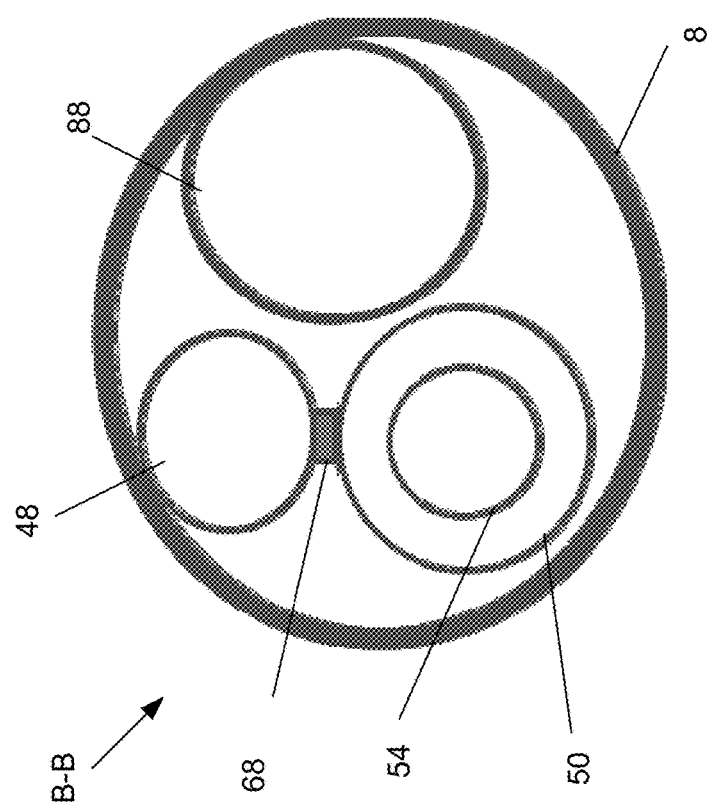

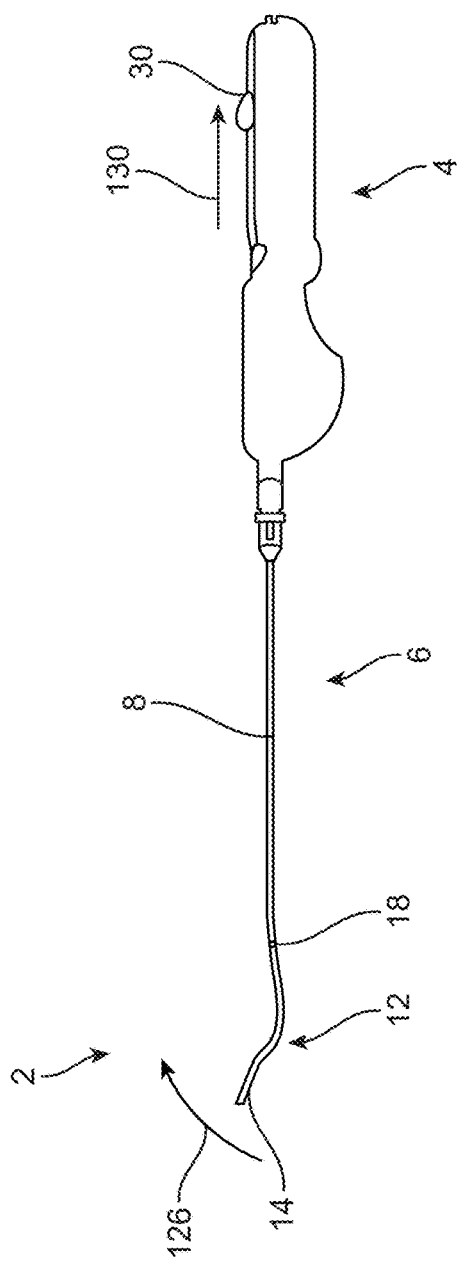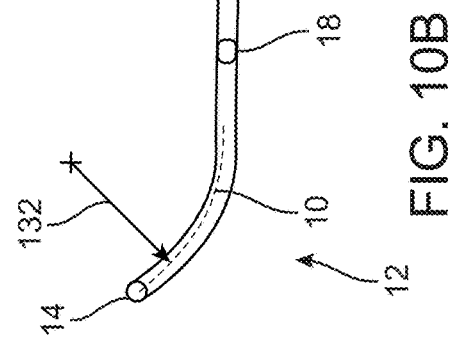

METHOD AND APPARATUS OF TUBAL PATENCY CATHETER AND DELIVERY SYSTEMS

This application claims priority to U.S. Provisional Application No. 62/005,355, filed May 30, 2014; U.S. Provisional Application No. 61/977,478, filed Apr. 9, 2014; U.S. Provisional Application No. 62/007,339, filed Jun. 3, 2014, and U.S. Provisional Application No. 61/902,742, filed Nov. 11, 2013, which are incorporated by reference herein in their entireties.

BACKGROUND

For assessing the inner morphology of the uterine cavity, or the patency of the fallopian tubes, physicians can utilize a variety of fluids and media for providing visualization during ultrasound and radiographic procedures. In some situations, the visualization quality of the ultrasonic imaging can be enhanced with additional echogenic constituents within the fluid media such as particles, air bubbles, $CO_2$ bubbles, and other contrasting materials that provide additional reflection and echogenicity for ultrasound. For uterine cavities, physicians evaluate the inner morphology of the cavity for the presence of disease while observing surrounding tissues and structures.

Fallopian tubes are potential spaces unless an intra-tubal insert is in situ, or in the presence of fallopian tube disease. These disease states can distort, occlude, or distend the fallopian tube walls in cases such as hydrosalphinges, inflammation, or when the culmination of bodily materials build up as deposits or detritus, or when remnants of previous ectopic pregnancies are present in the fallopian tube lumens. For assessing the inner morphology of the fallopian tubes, the patency of fallopian tubes, or the presence of tubal inserts, sufficient intra-uterine pressure needs to be generated to push or force the flow of media through the tubes. Literature indicates that the required amount of fluid pressure delivered at the endocervix through transcervical hysterosalpingography catheters to allow the flow of media through the fallopian tubes is on average 70 mmHg and pressure values using $CO_2$ or fluid media have ranged higher and lower than that average value.

A prior version for enhancing image quality utilizes the addition of a foaming agent or foam within a catheter system with subsequent injection into the uterine cavity. The foam is prepared by the operator through agitation of the foam and typically a fluid media such as saline. A catheter is introduced into the uterine cavity and a seal is created at the internal cervical os by a balloon or at the exocervix through the use of an occluding member or stopper at the cervical opening. The goal of these occluding devices is to maintain a seal within the uterine cavity so that sufficient pressure can be created through the injection of the foam/fluid media mixture to fill and distend the uterine cavity for inner surface examination. With additional pressure, up to the average 70 mmHg as reported in literature, the foam/fluid media mixture can infiltrate the fallopian tubes. Upon complete infiltration through the fallopian tubes and into the peritoneal cavity, the physician can make the assessment that the fallopian tubes are patent, or open, as evidenced by the spillage of fluid through the tubal lumen and into the peritoneal cavity or by visualization of bubbles traversing the fallopian tubes. This information can be useful for counseling women and couples for infertility and also for post-tubal insert implantation for permanent contraception. As an example, a foam agent can trap air particles or bubbles within a media prior to injection into the body. The foam mixture can be created manually by the operator by agitating a gel media with saline with two inter-connected syringes to create bubbles. Once turned to a foam consistency, the mixture is instilled into the body during sonographic procedures.

As an alternative, the art discloses the benefits of small sized gas bubbles for enhanced visualization of the fallopian tubes as well as the use of various gels and higher viscosity fluids for reducing the leakage of media out of the cervical canal during diagnostic uterine cavity procedures. The small sized gas bubbles, as one example, create greater sonographic reflections or echogenicity of the fluid during ultrasound diagnostic procedures.

Several uses of multiple syringe mechanisms for introducing two contrasting materials into a bodily cavity are known. For example, a first and second pump can supply sterile saline and micro-filtered air into the body for improved visualization during diagnostic procedures. The second pump filled with air is used to inject air into the saline and supplying the saline and air mixture into the body.

The use of two syringes: one syringe filled with a media comprised of small sized or micro-bubbles, and the other syringe filled with saline for simultaneous injection into the body is also known. The mixture is designed for improved visualization during sonographic procedures and evaluation of fallopian tube patency.

Yet another known method for enhancing visualization with ultrasound during fallopian tube diagnostic procedures uses a double barrel syringe for the injection of air and saline into the uterine cavity. When loading the system with saline, a second syringe barrel is drawing up room air. Once connected to a catheter and upon the depression of a plunger on the double barrel syringe, saline and air is combined at the base of the syringe through a y-fitting and then travels through the length of the catheter and into the uterine cavity. As the air bubbles combine with saline at the y-fitting, the coalescence of the bubbles occurs rapidly and echogenicity degrades as the air bubbles and saline traverse the length of the catheter. Importantly, the instructions for use in these double barrel catheter systems note that the bubbles employed in the media can create artifact while visualizing the uterine cavity since the bubbles may obscure anatomical features inside or on the inner cavity wall of the uterus.

In regards to bubble creation and venturi effect mechanisms, a micro bubble generating mechanism for shower heads is known. Other examples include nebulizing catheter systems for use in the pulmonary organs, and microparticulate introduction within perfluorocarbon liquid medications. A catheter with an aeration element within the distal end of the catheter for improving visualization within the uterine cavity and fallopian tubes is also known. Other applications depict a venturi mechanism attached to the proximal luer connector on the proximal portion of a catheter for the simultaneous infusion of air and saline within the uterine cavity.

A deflecting surface adjacent to the distal opening of an elongated catheter for directing a member or a fluid is known. As is an internal mandrel for selectively straightening a curved catheter for insertion into the uterine cavity. As another representative example of related art, a steerable catheter is known that provides articulation of the distal end.

Echogenicity can be altered (e.g., increased) with microbubbles or smaller bubbles. Ultrasound artifact by the presence of larger, obscuring air bubbles, can be reduced with the reduction of larger bubbles since the presence of the larger bubbles have been reported to obscure polyps or inner cavitary lesions.

SUMMARY OF THE INVENTION

An enhanced diagnostic visualization system for sonographic and radiographic imaging of the uterine cavity and fallopian tubes is disclosed. The system can be utilized in other natural or created bodily cavities and lumens. The system provides an integrated aeration device within a catheter for selectively providing echogenic air bubbles into a media that is injected into the body. The aeration device can be connected to a gas supply lumen that provides bubbles automatically to a flowing media without the need for special pumps, syringes, or other actuation members. Alternatively the air supply lumen can be connected to a gas source filled with CO2 or other gaseous mixtures suitable for use in the body as substitutes for room air. In addition, the air supply lumen can selectively be reduced or occluded by the physician or operator to reduce or eliminate the infusion of air in the media. The liquid can be water, saline, or other fluid used in imaging applications for evaluating interior structures in the body. Additional agents for improving visualization can be provided in the form of gels and foams that alone or in combination with fluid media can provide additional contrast and an enhanced visual image for the diagnostic procedure.

The system can utilize an integrated automatic aeration device or tool at the distal end of the catheter to facilitate ultrasonic, radiographic, and endoscopic visualization through the use of bubbles within the pathway of the delivered liquid. The aeration component can be selectively turned on or off by manual or actuated occlusion of the air supply lumen at the proximal end of the catheter.

The system can be self-contained or automated in that no other external component or apparatus needs to be attached to the device for the delivery or cessation of air bubbles. The system can have an integrated aeration device that can selectively utilize room air through a gas lumen that is contained within the catheter and terminates with an opening, for example a lateral gas port, to room atmosphere in the proximal section of the catheter or system handle.

The aeration device can be integrated into a catheter system that contains an insertion catheter on the distal end. A system handle can be connected to the proximal end of the catheter. Manipulation controls on the system handle can be operated by the operator or physician to manipulate the catheter and tools. The system handle can contain a fluid supply or reservoir, a fluid injection system or pump, and control knobs and buttons for actuating components on or in the catheter. For instance, the system handle can have a pump lever for manually injecting media from the fluid reservoir. The media can be sterile saline and/or other media such as contrast agents, foams, gels, and other media and fluid for use in the body for diagnostic sonographic and radiographic procedures. The control knobs on the handle can include buttons for changing the physical curvature of the insertion catheter, rotating the insertion catheter, advancing the length of the insertion catheter, and altering the aeration device by turning on, off, or reducing the flow of bubbles into the media. The bubbles can be turned off and restarted. The system handle can provide a one-handed procedure for the physician. One-handed operation can allow the freedom to use the other hand for manipulation of other instruments or operation of the diagnostic system like an ultrasound probe (either vaginal or abdominal) and the physical keyboard, joy stick, roller ball, or buttons of the ultrasound machine. The freedom to use the contralateral hand also provides the ability to palpate or manipulate the patient and specific patient anatomy while simultaneously performing the procedure without requesting for additional help from other resources or staff personnel. The handle can be configured to allow the physician to operate all of the catheter mechanisms with only one hand position and does not require the physician to alter, re-grip, or re-position his/her hand throughout the entire operation of the catheter system and procedure.

The aeration device can be integral to the catheter system for an automated injection of air bubbles in response to the flow of media through the aeration device. The aeration device can be self-contained and integrated within the insertion catheter without the need of secondary pumps or syringes. The aeration device can have a proximal lumen for accepting media from the fluid supply and a nozzle connected to the air supply. The flow of media (e.g., liquid) by the nozzle connected to the air supply pulls air into the flowing media and into a funnel at the distal end of the aeration device.

The aeration device can utilize the Bernoulli principle where the flow of media or fluid, with a known pressure, is forced through a flow restriction (a venturi). When passing through the restriction, the flow velocity of the fluid increases and the pressure within the fluid decreases. Contained in the restriction area of the aeration device is the nozzle opening of the air supply that is connected to an air supply lumen that can be selectively open to room air. The decrease in pressure in the fluid pulls or entrains room air gas, which is at a higher atmospheric pressure, into the flowing fluid which then passes through a funnel opening distal to the restriction with an opening angle less than 15 degrees. This is also known as a Venturi Effect. The system utilizes this principle as a built in component within the catheter system for supplying air bubbles into a flowing media used for sonographic and radiographic procedures. As such, the aeration of the flowing media is self-contained and integral to the catheter system for automatically supplying air bubbles when media is injected into the body, such as the uterine cavity and fallopian tubes.

The aeration device can be placed at a location in the catheter system immediately distal or at any point along the insertion catheter distal from the fluid supply source. For instance the aeration component can be integrated within the fluid supply system a centimeter from the fluid source outlet within the catheter system. In some configurations, placing the aeration component within the catheter system may reduce the overall diameter of the catheter that is being placed into the body. In other embodiments, the placement of the aeration component at the most distal location in the insertion catheter can provide additional benefits. The amount of air bubble coalescence is proportional to length of travel within the catheter system prior to exiting into the bodily cavity. Positioning the aeration component at the most distal end of the insertion catheter reduces the coalescence of these air bubbles. Once the flow of fluid passes through the aeration device, air bubbles can be entrained into the media and pass through the insertion catheter. The insertion catheter can have a distal opening (e.g., an outlet port) for placing the media into the body or uterine cavity. In practice, the insertion catheter is provided with a malleable distal section to facilitate manipulation and passage through the cervical canal. The distal end opening can have a slightly rounded or bulbous shape to reduce trauma and facilitate passage of the catheter through the cervix. A malleable section is advantageous for bending the distal section in the presence of anteverted or retroverted uteri, or stenotic cervical canals.

The catheter can be curved deliver the distal opening of the aeration device in close proximity to the fallopian tube ostia. The insertion catheter can be in a generally straight configuration for insertion or passage through the cervix. This straight portion at the distal end of the catheter can have an internal malleable section to facilitate passage of the insertion catheter through the cervix.

The aeration device can be located at the most distal location in the insertion catheter 1 to 9 millimeters to 1 to 4 centimeters prior to the opening at the distal end. This embodiment can mix the air into the media at a location immediately prior to injection into the body, thereby increasing the echogenicity of the media by reducing the time allowed for the air bubbles to coalesce into the media. FIG. 1 below demonstrates the principles in an aeration device within a distal angled ball tip of an insertion catheter. The aeration device can be constructed from softer durometer materials, such as 63 durometer polyether block amides (e.g., Pebax® from Arkema of Colombes, France) or polypropylene that allow for greater flexibility for inserting the device into a bodily cavity or lumen than higher durometer Pebax® or nylon. There are numerous choices for biocompatible polymers, metals, and material blends that can be substituted for this application.

The system can provide site specific, aerated media for information on the patency of individual fallopian tubes. This diagnostic information can be utilized in assessing infertility or determining the effectiveness of a tubal insert for permanent contraception. The entire procedure including the instillation of fluid, the directionality of the aerated media, the size of the aeration bubbles, the quantity of aeration bubbles, and the ability to turn the aeration feature on or off, can be actuated by the operator using one hand on the handle and one hand position on the proximal portion of the catheter. The system can be used to deliver drugs, therapeutic devices, and can collect a diagnostic specimen with collection mechanisms to and from target sites, such as bodily cavities, lumens, and fallopian tubes. The system can be used to deliver fallopian tube tools with ultrasound, radiographic, or endoscopic elements. The system can be utilized for the delivery of inserts and materials into the fallopian tube within a specific fallopian tube for enhancing echogenicity, or determination and identification of the fallopian tube lumen for the placement of the fallopian tube device. The system can allow for the staging of multiple fallopian tube devices through a tool lumen. The devices can be a cytology, cellular, or fluid sampling tool. The system can use an endoscope for visualization of the fallopian tube ostia with an integrated aeration system that provides on demand bubbles to allow for the direct visualization of lumen patency through the imaging of bubbles passing into the tubal ostia within distension media.

BRIEF DESCRIPTION OF THE DRAWINGS

FIG. 4 illustrates a variation of cross-section B-B.

FIG. 9 illustrates a variation of a method for rotating the distal end of the system.

FIG. 10a illustrates the distal end of the system in a straight configuration.

FIG. 10b illustrates the distal end of the system in a curved configuration.

DETAILED DESCRIPTION

Figure 1:
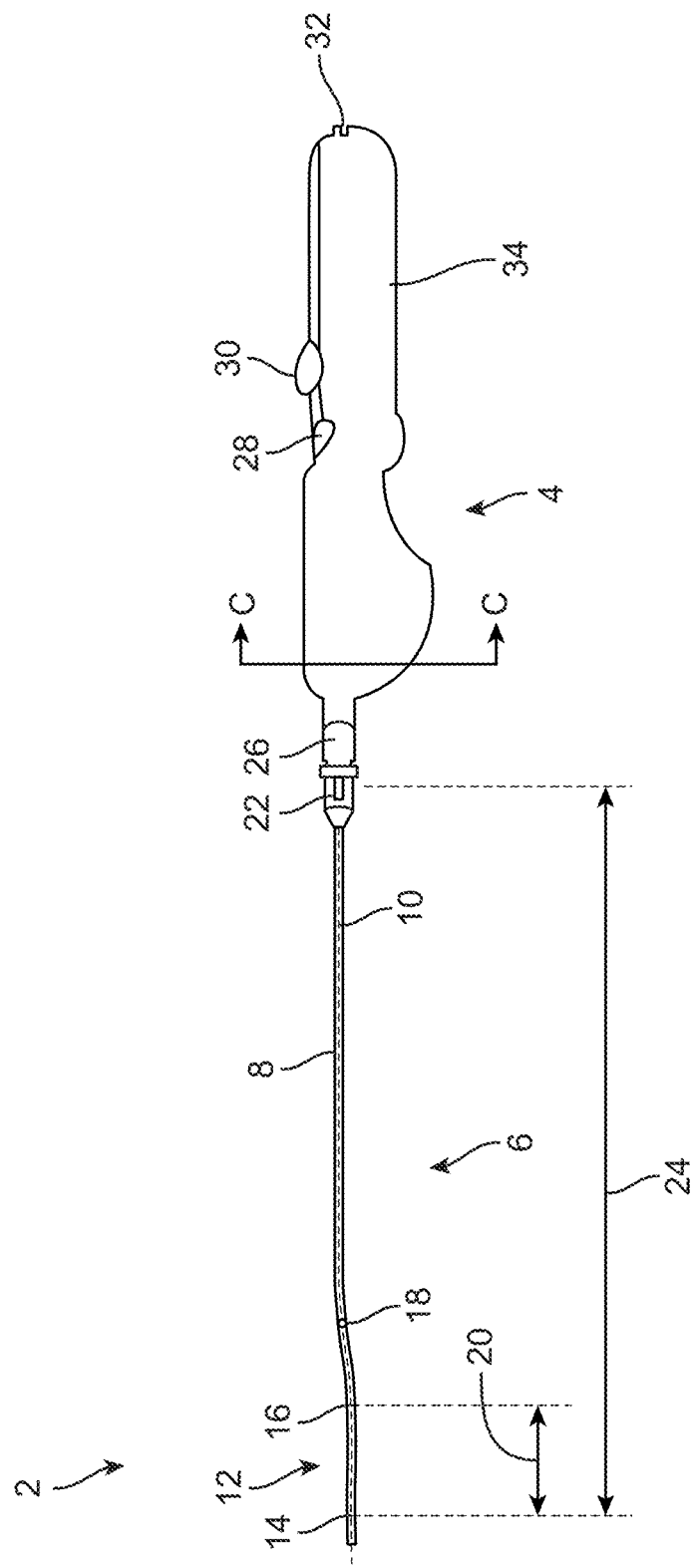
FIG. 1 illustrates a variation of the aeration system having a handle and an aeration device.

FIG. 1 illustrates that an aeration system 2 can have a system handle 4 and an aeration device 6. The aeration system 2 can be used to deliver aerated liquid 120 to a target site within a patient, for example, delivering saline infused with air bubbles within a uterus 140. The liquid can be aerated with air, carbon dioxide, nitrogen, oxygen, or combinations thereof.

The aeration device 6 can have a catheter 8. The catheter 8 can have a catheter longitudinal axis 10. The aeration device 6 can have one or more indicia markings 18, for example the catheter markings 18 in or on the catheter 8, and/or overtube markings 108 in, on, or under an overtube 102, described below. The indicia markings 18 can be visible, radiopaque, echogenic, or combinations thereof.

The catheter 8 can have a flexible or malleable distal tip 12. The distal tip 12 of the catheter 8 can have an outlet port 14 at or near the distal terminal end of the catheter 8. The distal tip 12 of the catheter 8 can have a gas inlet, such as a lateral gas port, in fluid communication through the catheter 8 with the outlet port 14. (The gas inlet can be on a non-lateral side of the system 2, such as extending from the proximal terminal end of the system handle 4, but is referred collectively herein as the lateral gas port 16.) The lateral gas port 16 can be an opening or orifice of the proximal opening of a gas lumen 48. The lateral gas port 16 can extend out of the lateral side of the catheter 8 and multiple lateral gas ports 16 are possible. The indicia marking 18 can be proximal to or longitudinally overlap with the lateral gas port 16. For example, the lateral gas port 16 can extend from the side of a catheter marking 18.

The length along the catheter longitudinal axis 10 from the lateral gas port 16 to the outlet port 14 can be an aeration length 20. The aeration length 20 can be the length from the introduction of gas into the liquid being delivered by the device (e.g., the location of the tap or throat of the venturi, discussed below) to the outlet port 14. The aeration length 20 can be, for example, from about 1 in. to about 9 in., more narrowly from about 1.5 in. to about 5 in., for example about 2 in. The aeration length 20 can be less than about 9 in., more narrowly less than about 5 in., more narrowly less than about 2 in.

The proximal terminal end of the aeration device 6 can have an aeration device connector 22. The aeration device connector 22 can be a widening of the catheter 8 and be placed on the catheter 8 adhesively, mechanically attached or bonded, secured by a clamp, a heat-shrink collar, or ring, threaded onto the catheter 8 by luer connectors, or combinations thereof. The aeration device connector 22 can be configured to attach to the system handle 4.

The aeration device 6 can have a device length 24 or catheter length from the distal terminal end (or outlet port 14) to the proximal terminal end of the aeration device 6. The device length 24 can be from about 6 in. to about 18 in., more narrowly from about 9 in. to about 12 in., for example about 10.5 in. The ratio of the device length 24 to the aeration length 20 can be from about 2:1 to about 10:1, more narrowly from about 3:1 to about 6:1, for example about 5:1. The ratio of the device length 24 to the aeration length 20 can be greater than about 2:1, more narrowly greater than about 3:1, yet more narrowly greater than about 5:1, yet more narrowly greater than about 10:1.

The distal terminal end of the system handle 4 can have a system handle connector 26. The aeration device connector 22 can be configured to attach to the system handle connector 26.

The system handle 4 can have actuators or controls for manipulating the shape, position, orientation, or combinations thereof of the distal tip 12 of the aeration device 6. The controls can be a rotation knob 28, deflection slide 30, of combinations thereof. The system handle 4 can have actuators or controls for the controlling the flow of air or gas within the aeration lumen, or the size and/or density of the air or gas bubbles within the aeration lumen. The controls can be a rotation knob 28, deflection slide 30, valve, or combinations thereof.

The system handle 4 can have an inlet port 32 configured to receive a liquid. The system handle 4 can have a pump lever 34 rotatably attached to the remainder of the system handle 4.

Figure 2A:
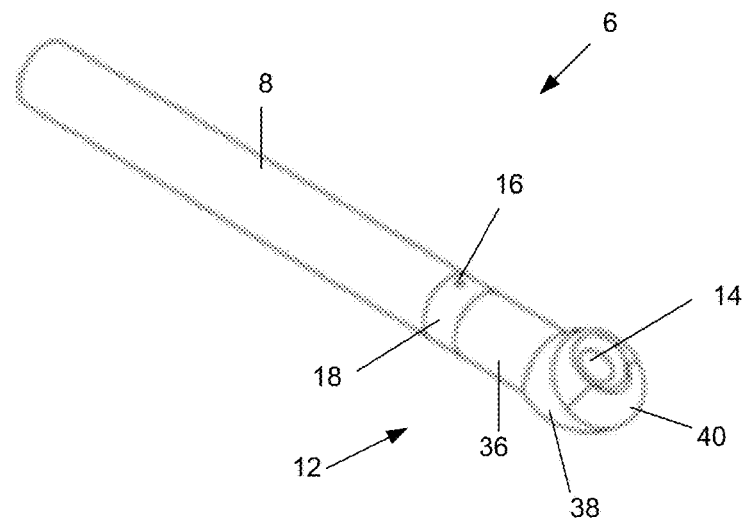
FIGS. 2a through 2c are perspective, top and side views of a variation of the aeration device.
Figure 2B:
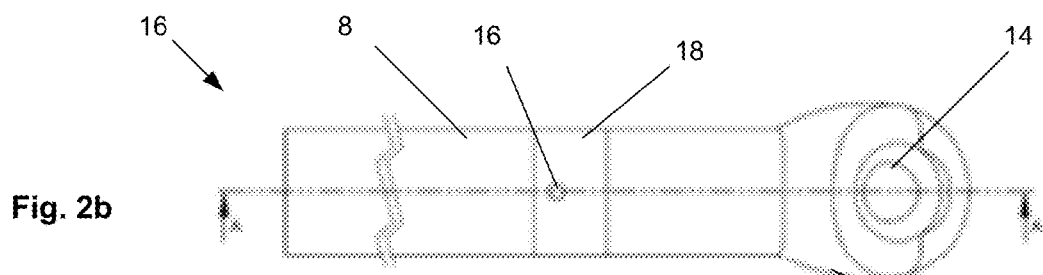
Figure 2C:
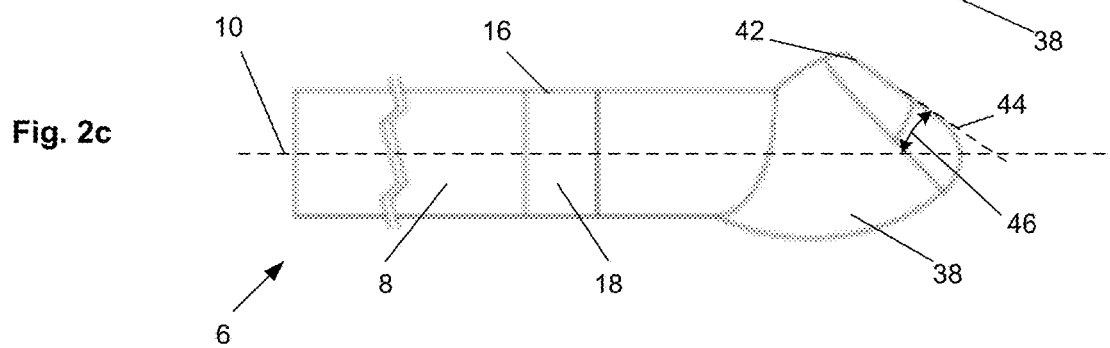

FIGS. 2a through 2c illustrate that the distal tip 12 can have a neck 36 of the catheter 8 attached to or terminating in a head 38 at the distal terminal end of the distal tip 12. The distal tip 12 can be straight in configuration with a rounded, smooth, atraumatic tip with an opened distal end, or side holes, or combination thereof. The head 38 can have a ball tip 40, an outlet port 14, and an outlet face 42 (i.e., distal end opening). The ball tip 40 can be rounded and atraumatic. The outlet port 14 can be recessed within the outlet face 42.

The outlet face 42 can extend along an outlet face plane 44. The outlet face plane 44 can intersect the catheter longitudinal axis 10 at an outlet face angle 46. The outlet face angle 46 can be from about 10° to about 90°, more narrowly from about 15° to about 45°, for example about 30°, also for example about 90° (i.e., perpendicular).

Figure 3A:
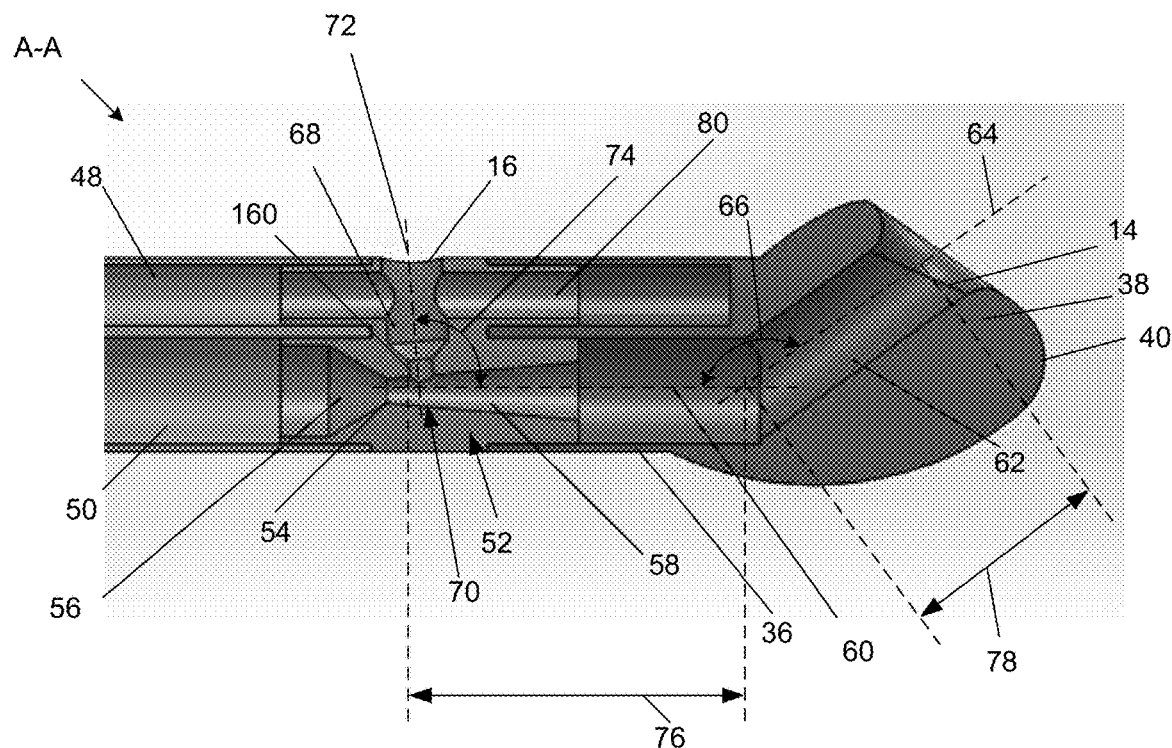
FIGS. 3a through 3d illustrate variations of partial lengths of cross-section A-A.

FIG. 3a illustrates that the catheter 8 can have the gas lumen 48 and a liquid lumen 50. The liquid lumen 50 can have a venture 52. The venture 52 can have a converging inlet nozzle 56 ending at a venturi constriction 54. The venturi constriction 54 can be the narrowest point or restriction in the venture 52. The venturi 52 can have a diverging outlet diffuser 58 extending distally from the venturi constriction 54. The liquid lumen 50 can have a liquid lumen longitudinal axis 60. The surface of the diverging outlet diffuser 58 can form from about a 10° angle to about a 30° angle, for example a 15° angle with the liquid lumen longitudinal axis 60.

The liquid lumen 50 can distally terminate at the outlet port 14. The liquid lumen 50 can distally terminate or merge into an outlet channel 62 in the distal tip 12 where the leading edge or head 38 of the insertion catheter 8 is located. The outlet channel 62 can have an outlet channel longitudinal axis 64. The outlet channel longitudinal axis 64 can intersect the liquid lumen longitudinal axis 60 at an outlet angle 66. The outlet angle 66 can be from about 0° (e.g., the outlet channel 62 can be a narrowing or widening of the liquid lumen 50) to about 90°, more narrowly from about 15° to about 45°, for example about 30°, also for example about 15°, also for example about 0°. The outlet angle 66 can be a non-zero angle. The diameter of the outlet channel 62 can be equal to, larger than, or smaller than the diameter of the liquid lumen 50.

The gas lumen 48 can be connected to an air supply, ambient air, or other gas supply. The proximal end of the gas lumen 48 can be attached to a pressurized gas source. The proximal end of the gas lumen 48 can be open to the environmental atmosphere or non-pressurized or low-pressurized gas source such as a small volume of gas within a rigid or flexible container.

A gas injector channel 68 can extend from the gas lumen 48 to the venture 52. The gas injector channel 68 can narrow at a nozzle or tap 160 where the gas injector channel 68 fluidly connects to the venturi 52 at a throat 70 of the venture 52. The throat 70 can be at the venturi constriction 54, distal to the venturi construction 54 (e.g., in the diverging outlet diffuser 58), proximal to the venturi constriction 54 (e.g., in the converging inlet nozzle 56), or combinations thereof. The gas injector channel 68 can extend through the lateral wall of the catheter 8 at the lateral gas port 16. The gas injector channel 68 can have no lateral gas port 16.

A filter, such as a micro-filter, or a check valve 94 or one-way valve, can be on the lateral gas port 16 and/or within the channel of the gas lumen 48. The micro-filter can be constructed with a porosity to provide a sterile air barrier, and supply sterile air bubbles into the fluid and to the target site (e.g., patient's body). The micro-filter can have a 3 micron porosity rating. The micro-filter can be used as a sterile air barrier or a mechanism to govern the amount of air flow within the air lumen. The micro-filter can have porosity levels, lower and higher than 3 micron, for example, to produce sterile air and the flow rate of about 1-10 ml/min of air bubbles into the fluid. The filter at the lateral gas port 16 or in the gas lumen 48 can filter fluid from entering the air lumen, for example for hydrophobic applications and/or when there is a risk of fluid or other unwanted liquids to get into the lateral gas port 16 or gas lumen 48. A check or one-way valve may eliminate the flow of pressurized fluids from the bodily cavity from entering into the air supply lumen and through the catheter system.

One or more lateral gas ports 16 can extend from the gas lumen 48 through the exterior catheter wall proximal to, distal to, or at the location of the gas injector channel 68. For example, a lateral gas port 16 can be located in the handle 4 (the gas lumen 48 and/or liquid lumens 50 can extend proximally into the handle 4), and the gas injector channel 68 can be located at the distal tip 12. The system 2 can have one or more gas injector channels 68, for example a first gas injector channel 68 in the handle 4 and a second gas injector channel 68 in the distal tip 12 of the device. One or more lateral gas ports 16 can also be selectively occluded or opened to increase, reduce, or eliminate the flow of gas within the fluid.

The gas injector channel 68 can have a gas injector longitudinal axis 72. The gas injector longitudinal axis 72 can intersect the liquid lumen longitudinal axis 60 at a tap angle 74. The tap angle 74 can be from about 170° to about 10°, more narrowly from about 90° (i.e., perpendicular) to about 135°, for example about 90°, also for example about 105°.

The aeration length 20 can be measured from the proximal end of the throat 70 or where the proximal end of where the tap 160 opens to the venture 52, along the respective liquid lumen longitudinal axis 60 and outlet channel longitudinal axis 64 to the outlet port 14. As shown, the total aeration length 20 can be the sum of the first partial aeration length 76 along the liquid lumen longitudinal axis 60 and the second partial aeration length 78 along the outlet channel longitudinal axis 64.

The distal end of the gas lumen 48 can terminate at the gas injector channel 68 or can have a gas lumen overrun 80 that extends distally past the gas injector channel 68. The gas lumen overrun 80 can have a closed distal terminal end in the catheter 8.

Figure 3B:
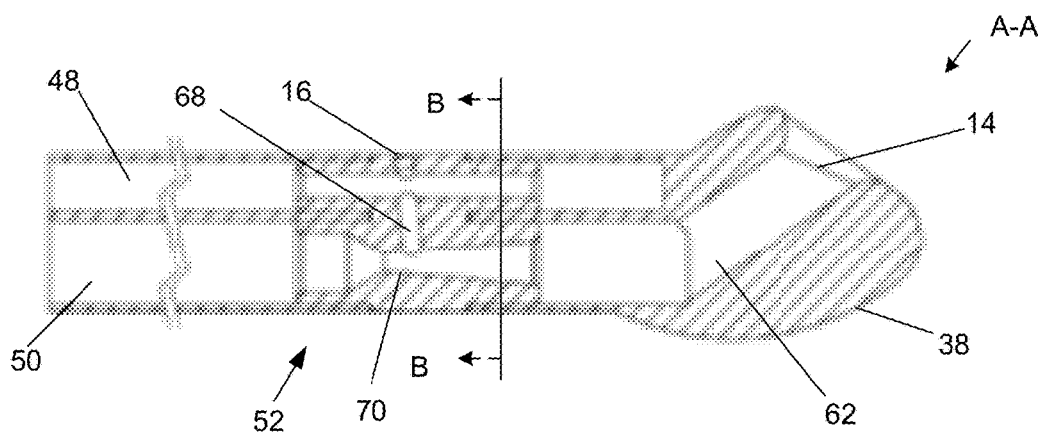

FIG. 3b illustrates that the gas lumen 48 can have a narrowed length at the lateral gas port 16 and/or gas injector channel 68. The gas injector channel 68 can be a constant radius, for example, the tap 160 is not narrowed with respect to the remainder of the gas injector channel 68.

Figure 3C:
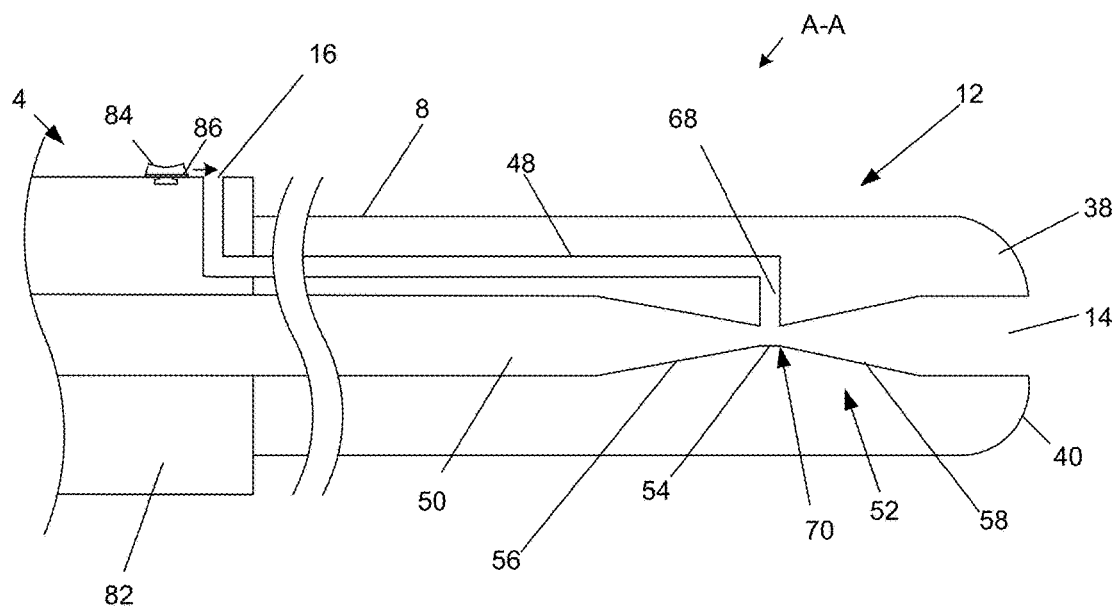

FIG. 3c illustrates that the system handle 4 can have a system handle case 82. The lateral gas port 16 can extend out of the side of the system handle case 82. The gas lumen 48 can extend from the lateral gas port 16, through the catheter 8 and to the gas injector channel 68. The throat 70 can be located at the venturi constriction 54. The system handle 4 case can have a gas slide 84. The gas slide 84 can have a cover 86 in contact with the surface of the system handle case 82. The cover 86 can be a sealing gasket, for example made from rubber, silicone, a polymer, or combinations thereof.

The gas slide 84 can be configured to translate, as shown by arrow, with respect to the system handle case 82 to cover or partially cover, and seal (or uncover and unseal, or partially unseal, when translated opposite to the arrow shown) the lateral gas port 16. When the gas slide 84 is in a position on the lateral gas port 16, the cover 86 can cover and seal the lateral gas port 16, preventing the gas (e.g., air) from flowing into the lateral gas port 16. The lateral gas port 16 can be releasably sealed by the user's hand, such as a palm, thumb, finger, or combinations thereof. The user can controllably aerate and not aerate the liquid flowing through the liquid lumen 50 by sealing and unsealing the lateral gas port 16.

The gas slide 84 and/or other controller can be mechanically connected to an occluding mandrel (i.e., an occluding member 122) instead or in addition to being positioned to slidably close the lateral gas port 16. The occluding mandrel can slidably occlude the gas injector channel 68 and/or the gas lumen 48. The gas slide 84 and/or other controller can also be configured to open and close a valve and/or inflate and deflate an occluding balloon in the gas lumen 48 or gas injector channel 68.

Figure 3D:
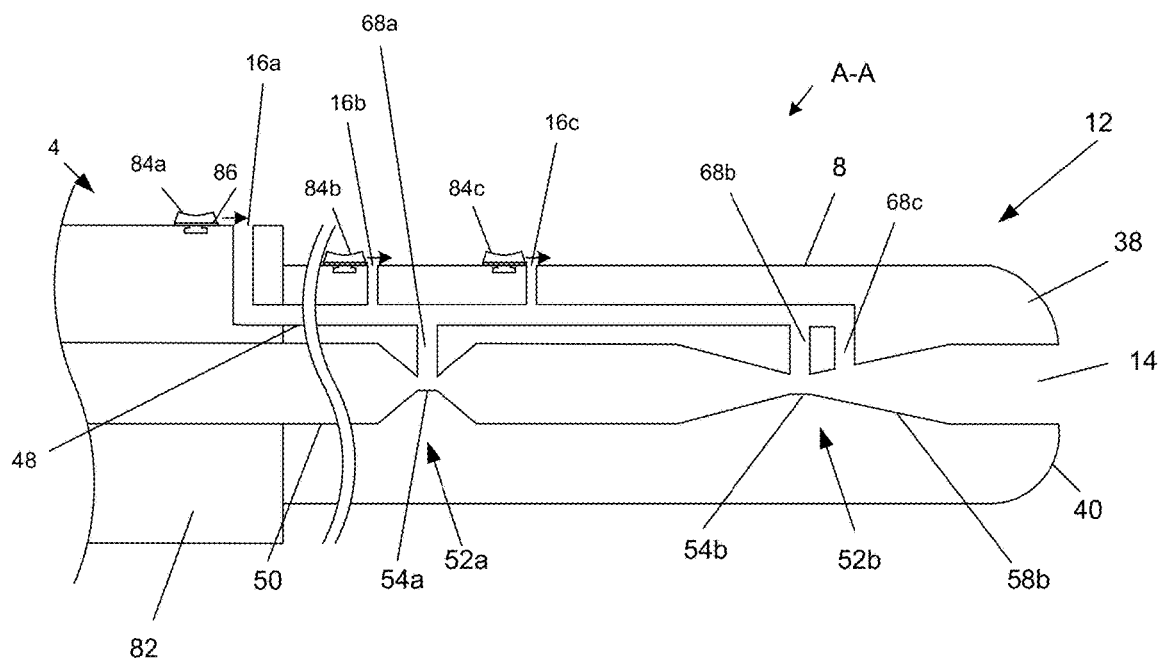

FIG. 3d illustrates that the system can have a first gas injector channel 68a, a second gas injector channel 68b, and a third gas injector channel 68c that can be connected to a single venturi 52 or to first 52a and second 52b (or more) venturis, respectively. The gas injector channels 68 can connect to the venturi(s) 52, for example, at the venturi constriction 54 and/or along the diffuser of the aeration device 6 to increase the amount of air bubbles to be entrained within the fluid media. As shown, the first gas injector channel 68 can connect to the first venturi 52a at a first venturi constriction 54a, the second gas injector channel 68b can connect to the second venture 52b at a second venturi constriction 54b, and the third gas injector channel 68e can connect to the second venture 52c at a second diverging outlet diffuser 58b. The gas injector channel 68s can branch off one air supply lumen, as shown. Alternatively, multiple air supply lumens with multiple openings within the restriction area of the aeration device 6 can be employed to increase the amount of air bubbles within the fluid media. The air supply nozzles can be placed in multiple locations circumferentially around the throat(s) 70.

The gas lumen 48 can have a first lateral gas port 16a, a second lateral gas port 16b, and a third lateral gas port 16c. For example, the second and third lateral gas ports 16b,16c can be on the catheter 8, as shown, or multiple lateral gas ports 16 can be on the handle 4. The first lateral gas port 16a can have a first gas slide 84a, the second lateral gas port 16b can have a second gas slide 84b, and the third lateral gas port 16c can have a third gas slide 84c. The gas slides 84 can slide, as shown by arrows, over the respective lateral gas ports 16 independently or concurrently, for example, if mechanically or electrically (e.g., via one or more motors or solenoids connected to the same controller) connected to each other.

The lateral gas ports 16 can be located along the catheter longitudinal axis 10 aligned or offset from the gas injector channels 68. For example, the third lateral gas port 16c can be between the first gas injector channel 68a and the second gas injector channel 68b.

FIG. 4 illustrates that the catheter 8 can have the gas lumen 48, the liquid lumen 50, and a tool lumen 88. A working tool (e.g., a biopsy tool, a scope, a sonogram probe, a cauterization tool, or combinations thereof) can be inserted through the tool lumen 88 and into the target site.

Figure 5:
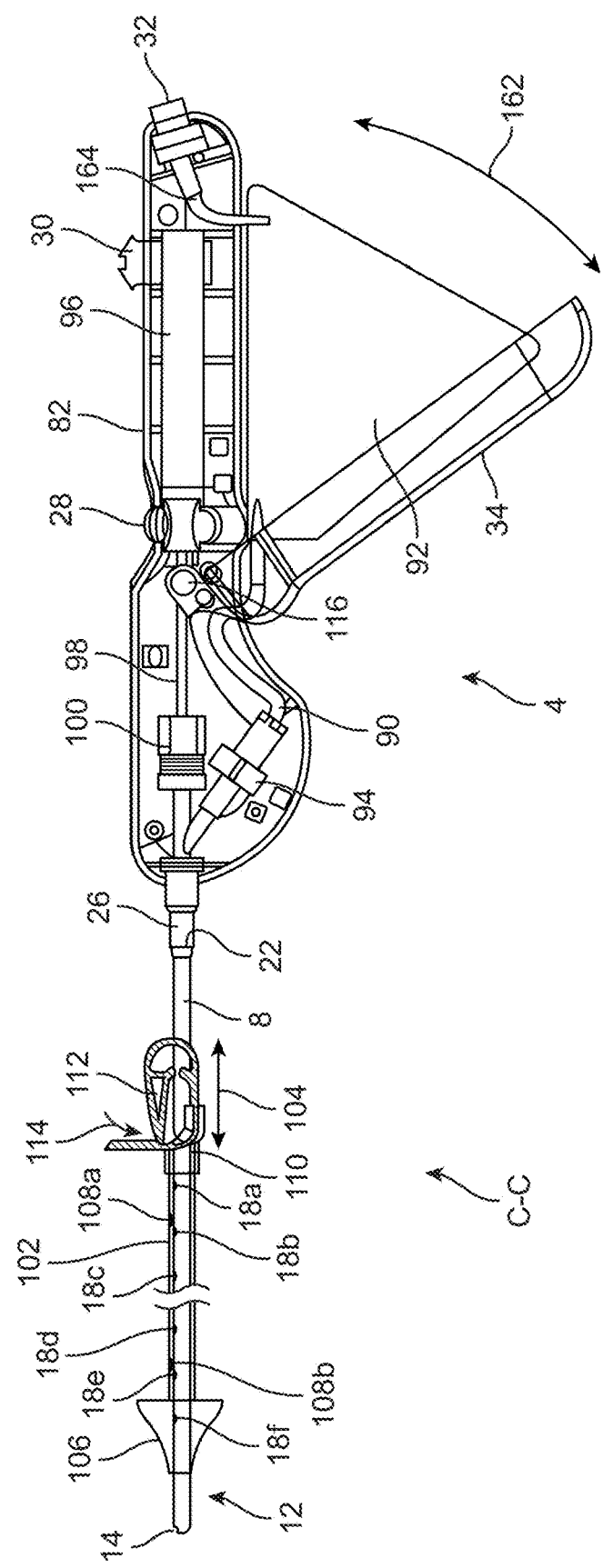
FIG. 5 illustrates a variation of a portion of cross-section C-C.

FIG. 5 illustrates that the system handle 4 can have an inlet port 32, an inlet-reservoir channel 164, and a flexible liquid reservoir 92 or fluid supply container. The inlet port 32 can be a female luer fitting and connection. The inlet port 32 can be in fluid communication through the inlet-reservoir channel 164 with the flexible reservoir. The liquid reservoir 92 can be between the rigid pump lever 34 and a rigid system handle case 82. The inlet port 32 can extend out of the proximal end of the system handle case 82. The inlet port 32 can be configured to attach to a liquid source (e.g., a hose, tube, or supplemental reservoir configured to deliver the liquid through the inlet port 32 and to the liquid reservoir 92). The inlet port 32 can have a check valve 94 or one-way valve configured to allow flow to the liquid reservoir 92 and prevent backflow (e.g., proximal flow from the liquid reservoir 92 and out the inlet port 32).

The system handle 4 can have a reservoir-liquid lumen channel 90, and an outlet valve, such as a liquid check valve 94. The liquid reservoir 92 can be in fluid communication through the reservoir-liquid lumen channel 90 with the liquid check valve 94. The liquid check valve 94 can be in fluid communication with the liquid lumen 90. The liquid check valve 94 can have a minimum cracking pressure, for example to allow fluid to flow to the liquid lumen 90 in the catheter 8. The liquid check valve 94 can be a one-way valve and can prevent backflow (i.e., from the liquid lumen 90 of the catheter 8 to the liquid reservoir 92).

The pump lever 34 can be rotatably attached to the system handle 82 case at a pump lever axle 116. When the liquid reservoir 92 contains liquid, the pump lever 34 can rotate away from the system handle case 82, as shown by pump lever rotation arrows 162, as the liquid reservoir 92 inflates. The pump lever 34 can be rotated toward the system handle case 82 to compress the liquid reservoir 92, for example, forcing liquid from the liquid reservoir 92, through the reservoir-liquid lumen channel 90, the outlet valve, the liquid lumen 50, the outlet port 14, and into the target site.

The pump lever 34 can provide a pumping action to supply aspiration to withdraw fluid and materials into a separate specimen container (not shown). A spring within the lever 34 can facilitate the pumping action of the lever 34 to open the lever 34 (not shown) for each compression.

The deflection slide 30 can be slidably attached to a slide canister 96. The slide canister 96 can be inside of and fixed to the system handle case 82. The rotation knob 28 and the deflection slide 30 can be attached to a steering rod 98. The steering rod 98 can extend through the system handle 4 and through the catheter 8. The proximal end of the catheter 8 can be attached to a hemostasis valve 100, for example a Tuohy-Borst adapter for allowing passage of the steering rod 98 without leaking fluid. The hemostasis valve 100 can fluidly seal the proximal end of the catheter 8. The steering rod 98 can extend through the hemostasis valve 100. The distal terminal end of the steering rod 98 can be fixed to the distal end of the inside of the catheter 8. The rotation knob 28 can rotate the steering rod 98 in the handle 4. The deflection slide 30 can translate the steering rod 98 in the handle 4.

The aeration device 6 can have an overtube 102 slidably positioned radially outside of the catheter 8. The overtube 102 can be translated and rotated with respect to the catheter 8, the translation shown by overtube-catheter translation arrow 104. The overtube 102 can be coaxial with the catheter 8. A stopper 106 can be attached to or integrated with the distal terminal end of the overtube 102. The stopper 106 can be flexible and made from a soft plastic, rubber, gel, or combinations thereof. The stopper 106 can be configured to seal the cervix 136 around the catheter 8, such as by plugging the external os of the cervix 136. During use, the stopper 106 can be positioned relative to the catheter 8 and longitudinally fixed to the catheter 8 to control the depth of the distal tip 12 in the cervix 136 and uterus 140.

The overtube 102 can be transparent, translucent, opaque, or combinations thereof. For example, the overtube 102 can have one or more overtube markings 108. An overtube first marking 108a can be at a proximal end of the overtube 102. An overtube second marking 108b can be at a distal end of the overtube 102. The overtube first and second markings 108a, 108b can be on the same side of the overtube 102 (e.g., an axis through the overtube first and second markings 108a,108b can be parallel with the catheter longitudinal axis 10.) The overtube markings 108 can be hollow markings, for example shaped as empty ovals or circles so the surface of the catheter 8 adjacent to the inside of the overtube marking 108 is visible.

The catheter 8 can have a catheter first marking 18a, catheter second marking 18b, and catheter third marking 18c at the proximal end of the catheter 8. The catheter 8 can have a catheter fourth marking 18d, catheter fifth marking 18e, and catheter sixth marking 18f at the distal end of the catheter 8. The catheter markings 18 can be collinear. The catheter markings 18 can be coplanar with the overtube markings 108.

The distances from the overtube first marking 108a to the overtube second marking 108b, from the catheter first marking 18a to the catheter fourth marking 18d, from the catheter second marking 18b to the catheter fifth marking 18e, and from the catheter third marking 18c to the catheter sixth marking 18f can be equal.

The overtube 102 can be translated relative to the catheter 8 to align the overtube markings 108 with the catheter markings 18 to control the position of the stopper 106 relative to the distal terminal end of the catheter 8. During use, the proximal markings can be visible outside of the patient (e.g., as visible markings) and the distal markings can be visible inside the patient (e.g., as echogenic markings viewed with a sonogram) and, for example, invisible from outside of the patient. The position of the overtube 102 first marking with respect to the first, second, and third catheter markings 18a, 18b,18c, can correspond to the position of the overtube second marking 108b with respect to the fourth, first, and sixth catheter markings 18d, 18e, 18f, respectively.

The proximal terminal end of the overtube 102 can be attached by a clip collar 110 to a releasable locking clip 112. The releasable locking clip 112 can fix to the catheter 8. The locking clip 112 can be fixed to the catheter 8 by rotating, as shown by arrow, a clip latch 114 into a locked position where the clip latch 114 presses against the catheter 8, friction fitting the locking clip 112 to the catheter 8. The releasable locking clip 112 can be unfixed from the catheter 8 by rotating the latch 114 in the opposite direction shown.

Methods for Using

Figure 6:
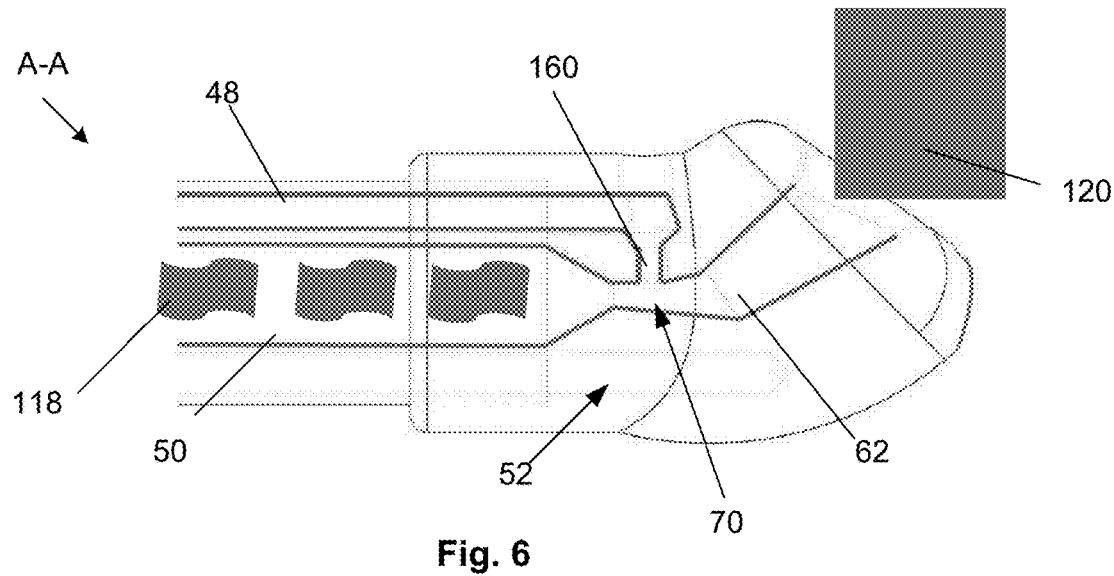
FIGS. 6 and 7 illustrate variations of cross-section A-A showing methods for using the aeration device.

FIG. 6 illustrates that non-aerated liquid 118 can flow distally through the liquid lumen 50 before the tap 160 or throat 70. When the non-aerated liquid 118 passes the tap 160 at the throat 70, the gas from the gas lumen 48 can enter the non-aerated liquid 118 via the tap 160, and aerate the liquid. The aerated liquid 120 can then pass through the outlet channel 62, out of the outlet port 14, and into the target site.

The aeration device 6 can be selectively turned on or off by the operator by use of an actuator, such as the gas slide 84 or button on the system handle 4 and/or proximal end of the catheter 8. The operator or physician can completely occlude or reduce the gas input to the gas lumen 48, for example, by sliding the gas slide 84 or cap, turning a valve, or combinations thereof, that can plug the lateral gas port 16. The user can manually occlude the lateral gas port 16 by closing the opening with his or her thumb, finger, palm or combinations thereof. The quantity of gas, and therefore, the amount of bubbles in the aerated liquid 120 can be selectively tuned or modulated (e.g., increased or decreased), for example depending upon the diagnostic visualization needs of the procedure.

The gas lumen 48 or opening of the gas injector channel 68 can be selectively opened or closed, for example by the occluding mandrel, to modulate the amount of bubbles in the aerated liquid 120. For example, the user can close the gas injector channel 68 or gas lumen 48 by sliding the occluding mandrel within the gas injector channel 68 by actuating the mandrel with a control, such as a slide or button, on the catheter 8 and/or system handle 4, or actuating and turning a valve at the opening of the gas injector channel 68 or in the gas lumen 48 by rotating a connecting rod and gear at the valve, or inflating an occluding balloon in the gas injector channel 68 or gas lumen 48 by use of a separate inflation lumen, or other implements that will pinch or close the gas injector channel 68.

In experiments, plugging or occluding the gas lumen 48 opening for a 50 cc injection of saline liquid resulted in no or a minimal amount of aspirated room air being collected in the aerated liquid 120 expelled from the catheter 8. In another demonstration of the system with the same 50 cc injection of saline liquid, for one half of the injection run, (i.e., 25 cc of saline), the gas lumen 48 was left unobstructed and was then obstructed for the injection of the remaining 25 cc of saline. The total volume of room air collected in the expelled aerated liquid was 2.25 cc or a 61% decrease in the amount of room air delivered in the aerated liquid 120.

The size of the gas (e.g., air) bubble or the total volume of gas (e.g., air) entering the liquid lumen 50 in the throat 70 can be controlled by the diameter opening of the gas injector channel 68. A larger diameter opening of the gas injector channel 68 can produce larger bubbles. In laboratory experiments, a 20% change in the tap 160 from a tap inner diameter of 0.016" to 0.020" resulted in an increase of total air volume being delivered in 50 cc of saline liquid at a rate of 100 mL/min from provided 5.75 cc of room air for the 0.020" ID compared to 3.8 cc of room air for the 0.016" ID, which is a 51% increase in total room air delivered in the aerated liquid 120.

Laboratory experiments indicated that obstructing the gas lumen 48 by 44% of the internal area of the gas lumen 48 by inserting an internal occluding mandrel within the gas lumen 48 up to 1 cm form the distal end of the device resulted in 4.0 cc of room air being collected in the expelled media at a 30% reduction of total room air delivered in the media.

The ability to reduce the quantity or rate of room air being injected into the target site, such as a bodily cavity, or the outlet channel 62 can improve visualization in certain bodily cavities like the uterine cavity 138 or reduce the possibility or occurrence of inducing an air embolism. The system can control the rate or volume of gas being injected into the body.

The lateral gas port 16 can be connected to a gas source such as a gas canister for the instillation of different gases such as $CO_2$. The gas canister can be attached or integrated within the system 2 or catheter 8, or connected via tubing from the gas source to the gas lumen 48. For example, the lateral gas port 16 can have a female luer fitting or tubing connection to the gas source. The bubbles within the aerated liquid 120 can be entrained, for example when the gas is $CO_2$.

The system 2 can use a pressurized or non-pressurized gas source. The gas source can be a low pressurized rigid or flexible container. The gas source can be transportable or fixed (e.g., a gas line from a central high-pressure source in a hospital extending from a wall). The low pressurized container can be a built-in or integrated component of the system 2. The gas, such as air or $CO_2$, can be supplied in a low pressure foil bag.

Gas, such as room air, can flow through the micro-filter in the lateral gas port 16 and/or gas lumen 48.

The liquid reservoir 92 can be filled with a liquid, foam and/or gel, such as saline or water. (Although described as liquid herein, the liquid lumen 50 can deliver foam and/or gel, and the description of the system and methods herein apply to liquids as it does to foams and/or gels.) The liquid can have or be supplemented with a drug, therapeutic agent, and/or surfactant. The liquid can be delivered through the inlet port 32 and check valve 94. The liquid reservoir 92 can be filled before and/or during the procedure delivering aerated 120 or non-aerated liquid 118 to the target site.

The gel can have a higher viscosity from a range of approximately 5% to about 75% to reduce the amount of leakage through the cervical canal or the fallopian tubes 142 to maintain distension within the uterine cavity 138. The system 2 can aerate the gel and/or foam, as described for the liquid. For example, an aerated gel can be delivered to the uterine cavity 138 and then an alternate solution with a lower viscosity than the gel, such as an aerated foam or aerated saline, can be delivered by the system 2 to the cornu for assessing patency of the fallopian tubes 142.

The drugs, such as anesthetic or therapeutic agents such as lidocaine, can be delivered to the liquid reservoir 92 alone or in combination with other liquids. The drugs, aerated or non-aerated, can be delivered to the target site. The system can nebulize the drug during delivery to the target site.

Increasing the ratio of surfactants in the liquid can increase the size and coalescence properties of the bubbles within the aerated liquid 120. Additional surfactant can create or entrain more bubbles in the aerated liquid 120 during use of the system. The use of a surfactant can be therapeutic. For instance, the surfactant can be baby shampoo, for example to improve the wetting properties or mucus removal action of aerated liquid 120 within nasal and sinus cavities.

The liquid lumen 50 can be connected to a vacuum source to remove media, including the delivered liquid, from the target site (e.g., a bodily cavity or lumen). The catheter 8 can have an aspiration lumen (e.g., the tool lumen 88 and/or liquid lumen 50 can be an aspiration lumen, or the catheter 8 can have a separate, devoted aspiration lumen). The pump lever 34 can be rotated to compress the liquid reservoir 92 and pump or deliver the liquid through the catheter 8 and to the target site.

The liquid reservoir 92 can be resilient and the pump lever 34 can be rotated outwardly from the system handle 4 case to expand the liquid reservoir 92, create suction or negative pressure in the liquid lumen 50, and draw aspirant from the target site and through the liquid lumen 50 into the liquid reservoir 92 or a separate specimen container.

Figure 7:
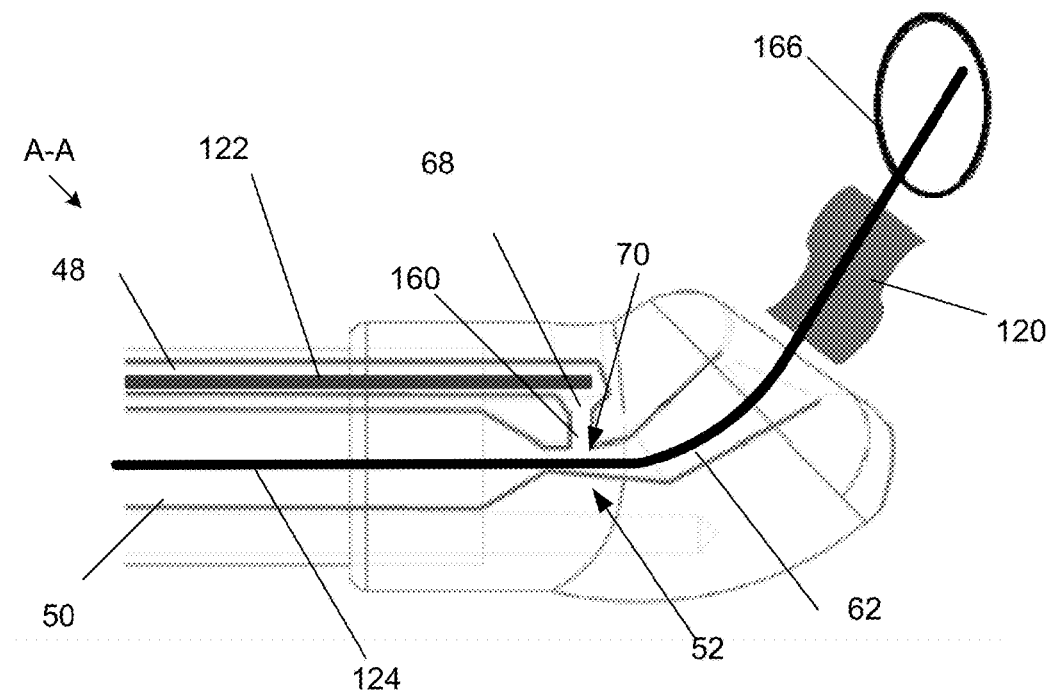

FIG. 7 illustrates that an occluding member 122 can be inserted through the gas lumen 48 to reduce or eliminate the amount of air within the gas injection lumen. The outlet port 14 of the distal tip 12 can be placed adjacent to the fallopian tube os 166, for example, for the passage of one or more tools 124, such as instruments for the delivery of fallopian tube inserts, endoscopes, or diagnostic fluid, cytology, or cellular sampling devices through the liquid lumen 50 and exiting the outlet channel 62. The openings for the introduction of one or more tools 124 within the liquid lumen 50 can be placed on or near the proximal handle 4 through the use of one or more Y-connector ports or valves.

Figure 8:
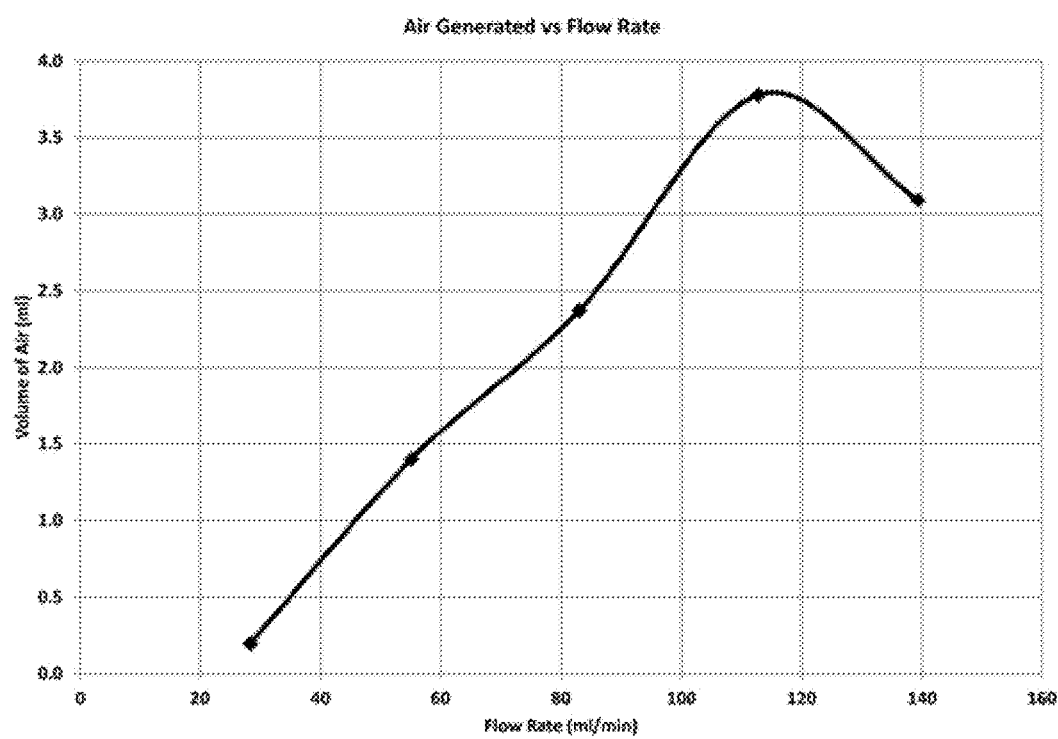
FIG. 8 is a graph of the ratio of the volume of air generated by a variation of the aeration system to the liquid flow rate through the system.

FIG. 8 illustrates that the amount of gas, such as room air, collected within the expelled aerated liquid 120 can be influenced by the rate in which the liquid, such as saline, is expelled through the liquid lumen 50 in the catheter 8 and ultimately, the rate the liquid is passing through the venturi constriction 54. The rate of liquid passage can impact the turbulence of the fluid flow. In laboratory experiments, as shown in FIG. 8, the amount of room air collected in the expelled aerated liquid 120 varies for differing flow rates through the catheter system. The gas lumen 48 can have flow regulators and/or valves that can provide accurate amounts of air within the liquid. In addition, FIG. 8 illustrates that a maximum amount of delivered air can be calculated as a result of flow turbulence in higher rates of flow.

The location of the aeration component, such as the gas injector channel 68, within the catheter 8 with respect to the output port 14 can impact the size of the bubbles of the gas in the liquid (e.g., saline). The gas can act as a contrast media (e.g., air), for example during ultrasound visualization. In laboratory experiments, the size of air bubbles within the aerated liquid 120 was observed to become larger for every 2.0 in. of traveled catheter length of the aerated liquid 120 due to bubble coalescence.

For visualizing the interior walls of the uterine cavity 138 via ultrasound, the presence of air bubbles, large or small, can provide an artifact in observing the inner morphology of the uterine cavity 138 for defects or abnormalities. The system can selectively reduce or eliminate air bubbles delivered to the target site via the liquid within the ultrasound procedure. The lateral gas port 16 can be manually occluded by the physician, for example with a finger. In laboratory experiments with the air supply lumen opening unobstructed and 50 cc of saline liquid injected at a rate of 100 mL/min from provided 5.75 cc of room air bubbles within the saline media collected. Within the same conditions with the air supply lumen opening obstructed at the proximal end of the catheter 8, no or a minimal amount of aspirated room air was collected within the expelled media (i.e., the liquid after exiting the outlet port 14).

FIG. 9 illustrates that the distal tip 12 can be curved or rotated, as shown by tip rotation arrow 126, for example when the deflection slide 30 is translated proximally 130, as shown by slide translation arrow 128, with respect to the system handle case 82.

FIG. 10*a* illustrates that distal tip 12 can have a straight configuration. The catheter longitudinal axis 10 can be substantially straight in the distal tip 12.

FIG. 10*b* illustrates that distal tip 12 can have a curved configuration. The catheter longitudinal axis 10 can have a catheter radius of curvature 132 from about 3 in. to about 36 in., more narrowly from about 6 in. to about 24 in.

Figure 11A:
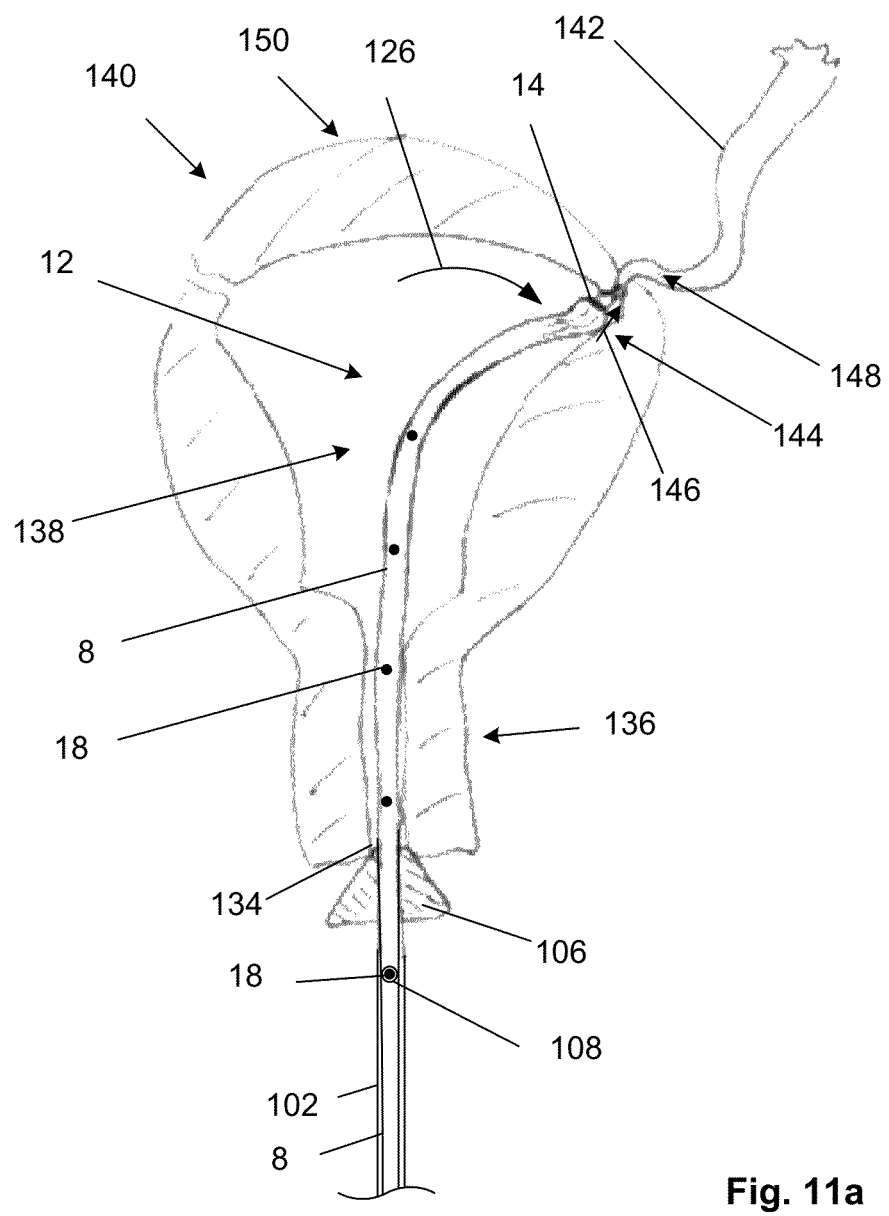
FIGS. 11a-c illustrates variations of methods for using the system.

FIG. 11*a* illustrates that the distal tip 12 of the catheter 8 can be introduced through the external cervical os 134, the cervical canal in the cervix 136, and positioned into the uterine cavity 138 where a diagnostic or therapeutic procedure can be accomplished. The visible catheter markings 18 on the distal portion of the catheter 8 can indicate the depth of insertion of the catheter 8 into the cervix 136 and uterine cavity 138.

The stopper 106 can be pressed against the external cervical os 134 or exocervix, creating a liquid-tight seal. When the stopper 106 is in a desired position with respect to the catheter 8, for example evaluated by the relative positions of the overtube markings 106 and catheter markings 18, the overtube 102 can be fixed to the catheter 8.

Intra-uterine pressure can be created or increased by the injection of fluid into the uterine cavity 138 by the outlet port 14 to distend or separate the walls of the uterus 140. In vivo, the uterine cavity 138 is typically a potential space. Uterine cavity 138 distension facilitates the visualization of the inner morphology of the cavity so that uterine abnormalities such as fibroids, myomas, polyps, or intra-uterine inserts like IUDs can be better visualized, diagnosed, and treated, for example by the system. The system can be used without the stopper 106, for example, not sealing the external cervical os 134. The system 2 can be used without distending the uterus 140. Not distending the uterus 140 improves patient comfort and this may be desirable for evaluations of fallopian tube inserts, or when specific anatomical features or devices or being evaluated, such as an IUD. Evaluating the fallopian tube os 166 142 can be facilitated with a curved distal catheter 8.

Once the cervical canal is traversed, the catheter 8, or a second catheter with a distal curved section, can be advanced further into the uterine cavity 138 and towards a corneal region. The second curved catheter can be selectively advanced, for example, by actuation of a sliding button, rod, or rotating gear.

Before or after the distal tip 12 is inserted into the uterus 140, the distal tip 12 can be curved or rotated, as shown by tip rotation arrow 126, to position the outlet port 14 at the target site, such as the cornu 144. The positioning of the distal terminal end of the catheter 8 and outlet port 14 at the cornu 144 can place the outlet port 14 in close proximity at a range of about 0 mm to about 3 mm to the fallopian tube ostia 166. For example, the outlet port 14 can be from about 0 mm to about 10 mm from the fallopian tube ostia 166, more narrowly from about 1 mm to about 5 mm, for example about 0 mm or about 1 mm.

The distal tip 12 can be configured to occlude or seal the opening of the fallopian tube os 166, for example to produce more distension pressure within the fallopian tube 142. For example, the ball tip 40 can have a generally bulbous shape. The ball tip 40 can have a larger diameter than the catheter 8 adjacent to the ball tip 40. The ball tip 40 can have an inflatable balloon with a central hole for the outlet channel 62. The ball tip 40 can be deflated and wedged or positioned into the patient's cornu 144, and then the ball tip 40 can be inflated, for example to seal the ball tip 40 at the cornu 144, containing pressure and maintaining distension in the fallopian tube 142.

The system 2 can aspirate material including liquid and solids from the target site through an aspiration lumen or the liquid lumen 50.

As shown by the aerated liquid flow arrow 146, the system can deliver aerated (and/or non-aerated 118) liquid 120 through the liquid lumen 50 and out the outlet port 14 to the cornu 144 and/or os of the fallopian tube 142, and/or inside of the fallopian tube 142. The aerated liquid 120 can have bubbles 148 that can coalesce in the liquid. The bubbles 148 can be visualized. The bubbles 148 can determine or confirm by ultrasound or other visualization whether the flow of liquid is traversing a specific fallopian tube 142. Flow of the bubbles 148 through the fallopian tube 142 can be evidence that the fallopian tube 142 is patent or occluded (e.g., by an occlusion device, ligation and/or disease).

Once the fluid has entered the fallopian tube 142, the aspiration lumen can suction and collect the fluid in the fallopian tube 142 by use of pumping action in the system handle 4 or by use of an external vacuum source connected to the aspiration lumen (e.g., liquid lumen 50, tool lumen 88, and/or gas lumen 48). A specimen collection cytology brush, bag, or other container can be located at the proximal portion of the aspiration lumen and collect the aspirated material such as fluid, for example for pathological examination. The collection of fluid from the fallopian tube 142 can be used for assessing fallopian tube disease, detecting cancerous ovarian cells, or aspirating materials or media that may reside in the peritoneal cavity.

The outlet port 14 can be offset from the distal terminal end of the device (e.g., the head 38 can be angulated, as shown in FIG. 3*a*), the ball tip 40 can be a leading blunt edge for the catheter 8. When the catheter 8 traverses the cervical canal, the leading ball tip 40 can atraumatically push the cervical canal and uterine cavity 138 open and not collect or scoop material into the outlet port 14.

The outlet port 14 can be at the distal terminal end of the device (e.g., the head 38 can be straight and at or near the central axis of the catheter 8, as shown in FIG. 3*b*). The head 38 can be the leading member of the device as opposed to the outlet port 14 of the catheter 8. When the catheter 8 traverses the cervical canal, the head 38, as the leading edge of the ball tip can push the cervical canal and uterine cavity 138 open and thereby minimize the materials that could be collected and/or gathered into the opening of the outlet port 14.

A lumen, such as the tool lumen 88, of the catheter 8 can be configured with an internal straightening or stiffening mandrel, such as the occluding member 122 or a straightening mandrel. The straightening mandrel can have a greater stiffness than the catheter 8 without the straightening mandrel. The catheter 8 can be biased, for example having a shape memory material, to a have a curved distal tip. The curve in the distal tip of the catheter 8 can be formed by thermal forming, molding, or heat setting the catheter material. The straightening mandrel can be inserted into and advanced along the catheter 8, extending into and/or through the distal tip 12, before or during insertion of the catheter 8 through the cervix 136. After the distal tip 12 traverses the cervical canal, the straightening mandrel can be retracted directly by pulling on the straightening mandrel or through the actuation of buttons, rods or gears on the system handle 4. As the straightening mandrel is retracted, the distal tip 12 can return to a curved shape, for example curving toward the cornu 144.

Figure 11B:
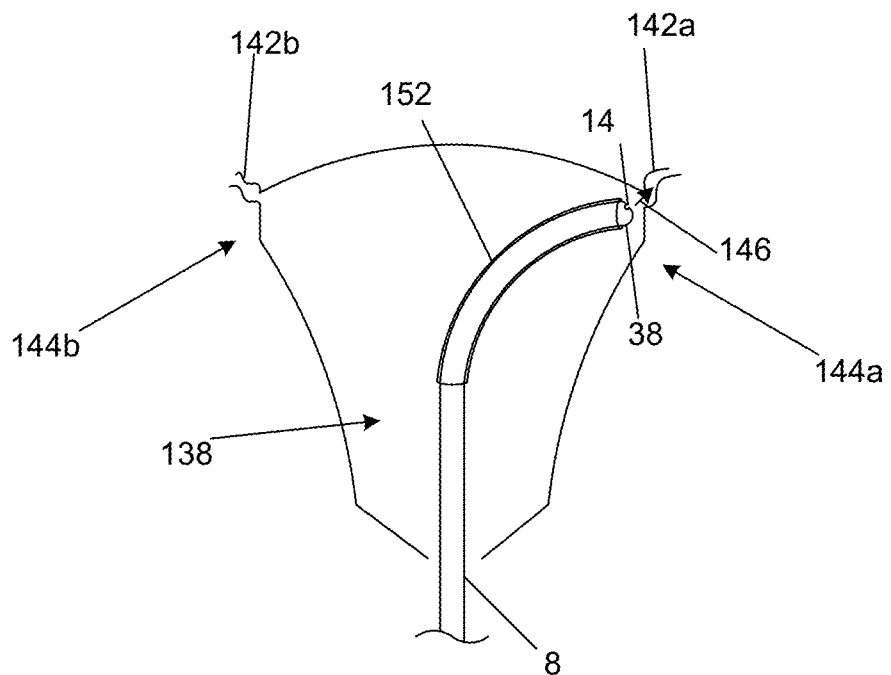
Figure 11C:
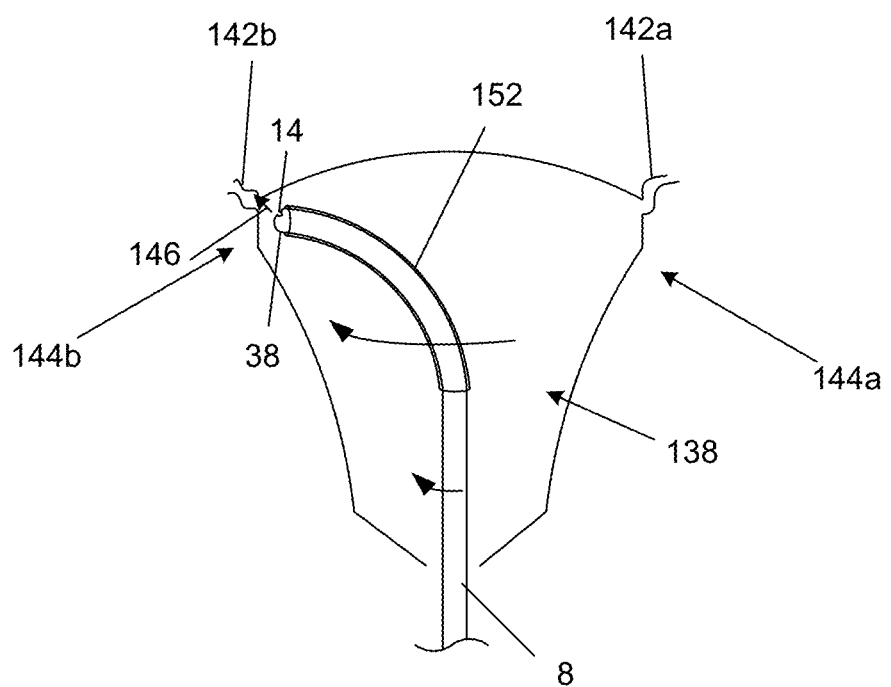

FIGS. 11b and 11c illustrate that a curved guide tube 152, curved overtube 102 or curved catheter 8 can be supplied with or within the primary catheter (i.e., the primary catheter is described elsewhere herein as the catheter 8). The curved guide tube 152 can be advanced directly or by sliding buttons, rods, or gears. Once the injection of air bubbles to the first fallopian tube os 166 is completed, the contralateral (i.e., second) fallopian tube 142b can be assessed, as shown in FIG. 11c, by retracting the curved guide tube 152 slightly, re-advancing the straightening mandrel, rotating the curved guide tube 152 180 degrees to the contralateral cornu 144, as shown by arrows, retracting the internal straightening mandrel (if used), and re-advancing the curved guide tube 152 and aeration device 6 towards the contralateral cornu 144.

The curved guide tube 152 can be rotated, as shown, manually by the physician through manual rotation of the entire catheter system, or through the turning of the rotation knob 28. The rotation knob 28 can be connected to the curved guide tube 152. The curved guide tube 152 can direct the primary catheter 8 to either cornu 144 of the uterine cavity 138. Each fallopian tube 142 can be diagnosed or treated individually. The aerated fluid can be released into the central body of the uterine cavity 138 or at the cornu 144.

The curvature of the catheter 8 can be controlled through the use of pull wires attached to an actuator on the handle 4, such as the rotation knob 28 and/or deflection slide 30. These actuators, such as the rotation knob 28 and/or deflection slide 30, can be gear wheels or cams that pull a steering or deflection wire connected to the distal end of the catheter 8, creating tension in the steering wire and catheter 8 that can curve the catheter 8.

The aeration device 6 can place air bubble-filled liquid within the fallopian tube ostia 166. The outlet port 14 can direct the liquid at an upward angle, such as the outlet angle 66, relative to the catheter longitudinal axis 10, in a cranial direction of the patient. The upward angle of the outlet port 14, or angled ball tip 40, can position the air bubble-filled (aerated) liquid 120 immediately at or towards the ostia openings of the fallopian tubes 142 with the catheter 8. When the catheter 8 is placed in the cornu 144 of the patient's uterine cavity 138, the catheter longitudinal axis 10 can be pointed towards the lateral wall of the uterus 140. The aeration device 6 can direct the air bubble-filled liquid in the cranial direction of the patient's uterine fundus 150 which can be the location of the patient's fallopian tube opening within the intramural or interstitial portion of the uterus 140.

The system 2 can be operated with one hand to inject liquid through the liquid lumen 50, advance and retract the straightening mandrel, advance, articulate and rotate (e.g., to direct the catheter 8 to a specific cornu 144) the catheter 8 with the rotation knob 28, deflection slide 30, buttons, gears, and/or cams, control the amount and/or density of air bubbles in the aerated liquid 120, or combinations thereof without re-gripping or re-positioning the hand on the system 2.

The device and features of the integrated aeration device 6 can be used in other natural or created bodily cavities or lumens such us the urethra, gastrointestinal tract, and others locations in the body.

The flow of bubbles can be tracked to and possibly through the fallopian tubes 142 to determine the presence and effectiveness of tubal inserts or tubal ligation for permanent contraception, determining the presence of unilateral fallopian tube disease, or combinations thereof. The use of Doppler ultrasound can facilitate the visualization of fluid and bubble flow through the fallopian tubes 142.

The system 2 can deliver devices to the fallopian tube 142 during ultrasound, radiographic, and endoscopic visualization to monitor the system position, procedural progress, and diagnostic information. The system 2 can enter the fallopian tube orifice or os with or without uterine distention for visualization. The uterine cavity 138, including the uterine fundus 150, can be in natural flaccid, substantially untensioned state (e.g., reducing the tendency for fallopian tube spasm) during use of the system 2. (Fallopian tube spasm can reduce the cannulation rate in the delivery of fallopian tube devices by hindering the passage of catheters 8 and devices.) The system 2 can be used to deliver inserts through the tube lumen into the fallopian tubes 142.

The bubbles 148 can create echogenic reflections, and therefore images, during ultrasound visualization. The bubbles 148 can create radiographic images during radiographic visualization, such as fluoroscopy. The movement of the bubbles 148 can be tracked by ultrasound and/or radiographic imagining as they progress into the fallopian tubes 142. By depressing, squeezing, or rotating the lever 34 of the pump handle and concurrently allowing the lateral gas port 16 to remain open, the bubbles 148 in the aerated liquid 120 can be used to direct placement of the device, for example by enhancing the visualization capabilities of the user.

A visual spectrum endoscope having a camera (e.g., CCD, CMOS) can be inserted through the tool lumen 88, or adjacent to the catheter 8, and to the target site. The uterus 140 can be distended, for example by inflation with the liquid or gas, for example opening the uterine cavity 138 to allow panoramic views of the uterine cavity 138 with the endoscope camera. The endoscope can have an outer diameter from about 0.4 mm to about 2.0 mm. The uterus 140 can be left undistended as the endoscope passes through and visualizes the uterine cavity 138, cornu 144, and fallopian tube os 166. The catheter 8 can inject liquid to the undistended uterus 140 (e.g., at the cornu 144 or os of the fallopian tube 142) to create local inflation around (e.g., within 10 mm of) the outlet port 14 to open the potential space and expand the range of the field or depth of view of the endoscope camera. The endoscope camera can be positioned adjacent (e.g., within 3 mm) of the outlet port 14. The endoscope can view the flow of bubbles 148 into the fallopian tube ostia 166 supplied selectively or on demand by the physician. The flow path of the bubbles 148 can indicate that the lumen or object immediately within the field of view of the endoscope is the fallopian tube ostia 166. (e.g., Within the uterine cavity 138, many objects can appear to be the fallopian tube 142 lumen even with high resolution endoscopes with full uterine distension and large fields of view.) The system 2 can deliver a tool 124 or fallopian tube instrument concurrent with bubbles 148, for example, to confirm the location and identity of the fallopian tube 142, as well as give the endoscopic viewer a sense of patency or fluid flow through the observation of a visual stream of bubbles into the fallopian tube lumen.

A tool 124 can be delivered through the liquid lumen 50, the gas lumen 48, or the tool lumen 88 of the catheter 8.

Figure 12A:
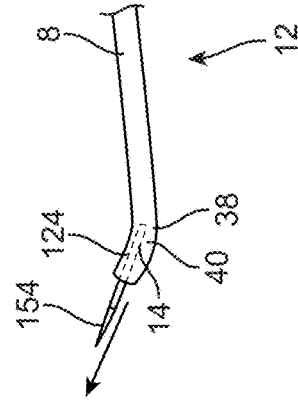
FIGS. 12a through 12c illustrate a method for deploying a tool through the system.
Figure 12B:
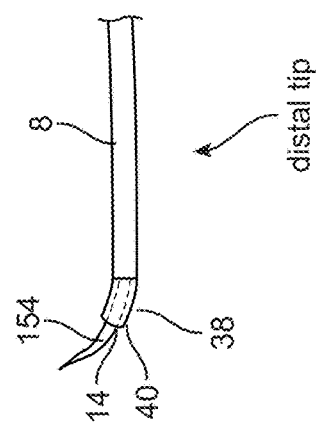
Figure 12C:
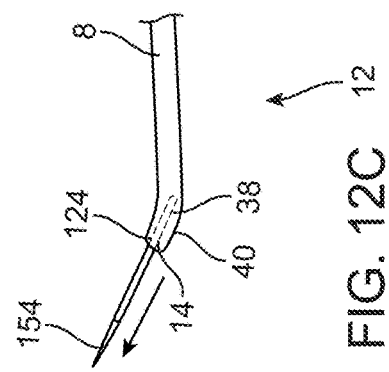

FIGS. 12a through 12c illustrate that a tool 124 can be delivered through the tool lumen 88 and out of the head 38 of the catheter 8. The tool 124 can exit the catheter 8 at the outlet port 14 or through a separate tool exit port. The tool 124 can be or be attached to an implant such as an intratubal insert 154 or fallopian tube insert. For example the intratubal insert 154 can be releasably attached to the distal terminal end of the tool 124. The tool 124 and insert can be translated out of the distal end of the catheter 8, for example, parallel with the catheter longitudinal axis 10 or deflected in an upward or cranial direction upon exiting the distal end of the catheter 8 (as shown). The intratubal insert 154 can be delivered into the fallopian tube 142 and then released from the tool 124. The intratubal insert 154 can be left in the fallopian tube 142 and occlude the fallopian tube 142 (e.g., immediately and/or through a healing response from the fallopian tube tissue).

Figure 13:
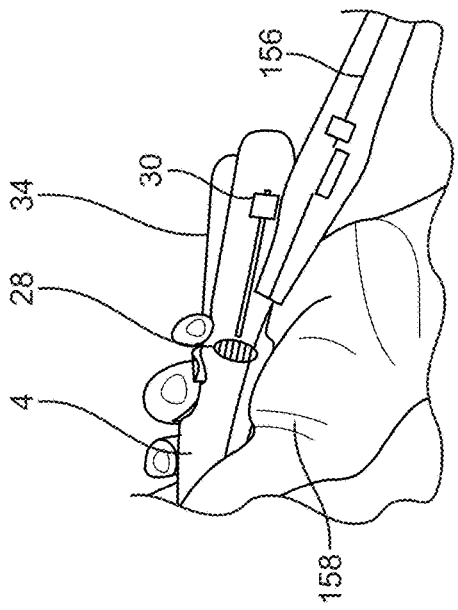
FIG. 13 illustrates a variation of a method for using a tool concurrent with the system.

FIG. 13 illustrates that the proximal end of the tool 124 can be connected to a tool handle 156. The tool handle 156 can control the tool 124, for example, steering, deflecting, extending, and retracting the tool 124, and controlling the release and/or reattachment to the intratubal insert 154. The tool 124 can be inserted through a terminal proximal opening of the tool lumen 88. A first hand 158 can be used to hold and operate and manipulate the system, for example the system handle 4, rotation knob 28, pump lever 34, and deflection slide 30. A second hand (not shown) can be used to operate and manipulate the tool handle 156, for example controlling the tool 124 and delivering the intratubal insert 154 to the fallopian tube 142. Either or both hands 158, or parts thereof such as the fingers, thumbs or palms, can be used to control gas flow into the gas lumen 48, for example by covering (i.e., closing) and uncovering (i.e., opening) the lateral gas port 16 on the system handle 4 and/or catheter 8.

The intratubal insert 154 can be delivered through the liquid and/or gas lumen 50,48.

The intratubal insert 154 can be releasably attached to a tool 124 in the system 2. The intratubal insert 154 can be in the delivery mechanism and can be advanced by use of an actuator on the handle 4. The actuator can be gear wheels which roll the insert out of the outlet port 14 of the catheter 8, a slideable button that manually advances the insert beyond the outlet port 14 and into the fallopian tube 142, a rotating knob 28 that engages a threaded piston for advancing the insert 154, other combinations of mechanical actuators for advancing a device in a catheter 8, or combinations thereof. An electrical, battery powered, or pressurized mechanism can advance the insert 154.

The system 2 can have two intratubal inserts 154, for example, to deliver one insert 154 to each fallopian tube 142 of a patient.

The delivery device can be integrated with a sampling device or cytology brush for pathological examination of the fallopian tube lumen. The sampling can be done with an aspiration lumen for removing materials from the fallopian 142 for further examination. The aspiration lumen can be fitted with an irrigation source to first instill fluid into the fallopian tube lumen and then remove the fluid media for subsequent pathological analysis. The fluid media can alternatively be supplied by the internal fluid pathway within the aeration mechanism (venturi 52).

The delivery device system can be used to deliver drugs, therapeutic agents, or biological material such as reproductive materials, into the fallopian tube 142.

The system 2 can instill $CO_2$ for the delivery of distension media into the peritoneal cavity. This would obviate the need to puncture the abdominal wall with a Veress needle prior to laparoscopic examination in the patient with suspected difficulty in gaining peritoneal access due to anatomy, obesity, abdominal adhesions, prior surgery, or other indications.

The system can deliver, for example through the tool lumen 88, fallopian tube inserts for the purpose of creating permanent occlusion and contraception. One such insert is the Essure™ product offered by Bayer HealthCare Pharmaceuticals Inc. The system 2 can deliver drugs, an aspiration element (e.g., by vacuum pressure or negative pressure), biopsy brush, sampling devices, or combinations thereof to the uterus 140 or fallopian tube 142 for the evaluation of ovarian cancer, endometriosis and other gynecological and reproductive disorders.

U.S. patent application Ser. No. 13/830,202, filed Mar. 14, 2013 is incorporated by reference herein in its entirety.

It is apparent to one skilled in the art that various changes and modifications can be made to this disclosure, and equivalents employed, without departing from the spirit and scope of the invention. Elements of systems, devices and methods shown with any embodiment are exemplary for the specific embodiment and can be used in combination or otherwise on other embodiments within this disclosure. Furthermore, unless specified otherwise, the elements of methods described can be performed in various orders, not just the disclosed order.

We claim:

1. A method for delivering an aerated liquid to a target site comprising:
    delivering a liquid through a first lumen in a catheter, wherein the first lumen has a venturi;
    delivering a gas to a second lumen in the catheter from an ambient gas supply;
    channeling the gas from the second lumen to the first lumen during the delivering of the liquid;
    mixing the gas with the liquid in a throat of the first lumen resulting in aerated liquid;
    delivering the aerated liquid out of an outlet port on the catheter, wherein the outlet port is less than 9 inches from a location of the channeling of the gas to the first lumen; and
    controllably stopping the delivering of the gas, wherein the controllably stopping the delivering of the gas comprises covering a gas port on a lateral side of a handle attached to the catheter, and wherein the covering comprises placing a hand on the gas port.

2. The method of claim 1, further comprising delivering an implant through the catheter, and deploying the implant to the target site.

3. The method of claim 1, further comprising controllably restarting the delivering of the gas.

4. The method of claim 1, wherein the target site comprises a uterine cavity.

5. The method of claim 1, further comprising curving the catheter to a cornu of a uterine cavity.

6. The method of claim 1, wherein the delivering the liquid comprises rotating a lever on the handle attached to the catheter, and wherein the rotating the lever comprises compressing a reservoir.

7. The method of claim 1, further comprising straightening the catheter.

8. The method of claim 1, further comprising delivering a drug to the target site.

9. The system of claim 1, wherein the outlet port is less than 5 inches from the location of the channeling of the gas to the first lumen.

10. The system of claim 1, wherein the outlet port is less than 2 inches from the location of the channeling of the gas to the first lumen.

11. The system of claim 1, wherein a ratio of a length of the catheter to a length from the outlet port to the location of the channeling of the gas to the first lumen is greater than 2:1.

12. The system of claim 1, wherein a ratio of a length of the catheter to a length from the outlet port to the location of the channeling of the gas to the first lumen is greater than 3:1.

13. A method for delivering an aerated liquid to a target site comprising:
- delivering a liquid through a first lumen in a catheter, wherein the first lumen has a venturi;
- delivering a gas to a second lumen in the catheter from an ambient gas supply;
- channeling the gas from the second lumen to the first lumen during the delivering of the liquid;
- mixing the gas with the liquid in a throat of the first lumen resulting in aerated liquid;
- delivering the aerated liquid out of an outlet port on the catheter, wherein the outlet port is less than 9 inches from a location of the channeling of the gas to the first lumen; and
- controllably stopping the delivering of the gas, wherein the controllably stopping the delivering of the gas comprises covering a gas port on a lateral side of a handle attached to the catheter, and wherein the covering comprises placing a cap on the gas port.

14. The method of claim 13, further comprising delivering an implant through the catheter, and deploying the implant to the target site.

15. The method of claim 13, further comprising controllably restarting the delivering of the gas.

16. The method of claim 13, wherein the target site comprises a uterine cavity.

17. The method of claim 13, further comprising curving the catheter to a cornu of a uterine cavity.

18. The method of claim 13, wherein the delivering the liquid comprises rotating a lever on the handle attached to the catheter, and wherein the rotating the lever comprises compressing a reservoir.

19. The method of claim 13, further comprising delivering a drug to the target site.

20. A method for delivering an aerated liquid to a target site comprising:
- delivering a liquid through a first lumen in a catheter, wherein the first lumen has a venturi;
- delivering a gas through a second lumen in the catheter;
- channeling the gas from the second lumen to the first lumen during the delivering of the liquid;
- mixing the gas with the liquid in a throat of the first lumen resulting in aerated liquid;
- delivering the aerated liquid out of an outlet port on the catheter, wherein the outlet port is less than 9 inches from a location of the channeling of the gas to the first lumen; and
- controllably stopping the delivering of the gas, wherein the controllably stopping the delivering of the gas comprises covering a gas port on a lateral side of a handle attached to the catheter, and wherein the covering comprises placing a hand on the gas port.

* * * * *

UNITED STATES PATENT AND TRADEMARK OFFICE
CERTIFICATE OF CORRECTION

PATENT NO. : 10,034,986 B2  
APPLICATION NO. : 14/495726  
DATED : July 31, 2018  
INVENTOR(S) : Matt Yurek et al.

Page 1 of 1

It is certified that error appears in the above-identified patent and that said Letters Patent is hereby corrected as shown below:

In the Claims

Column 20 In Claim 9, Line 62, please replace "The system of" with --The method of--.

Column 20 In Claim 10, Line 65, please replace "The system of" with --The method of--.

Column 21 In Claim 11, Line 1, please replace "The system of" with --The method of--.

Column 21 In Claim 12, Line 5, please replace "The system of" with --The method of--.

Signed and Sealed this  
Fourth Day of June, 2019

Andrei Iancu  
*Director of the United States Patent and Trademark Office*